(12) United States Patent
Ridley et al.

(10) Patent No.: US 8,761,862 B2
(45) Date of Patent: Jun. 24, 2014

(54) ULTRASOUND GUIDED PROBE DEVICE AND STERILIZABLE SHIELD FOR SAME

(76) Inventors: Stephen F. Ridley, Columbia, SC (US); M. Dexter Hagy, Greenville, SC (US)

(*) Notice: Subject to any disclaimer, the term of this patent is extended or adjusted under 35 U.S.C. 154(b) by 1140 days.

(21) Appl. No.: 12/576,487

(22) Filed: Oct. 9, 2009

(65) Prior Publication Data

US 2011/0087105 A1 Apr. 14, 2011

(51) Int. Cl.
*A61B 5/05* (2006.01)

(52) U.S. Cl.
USPC ........... 600/427; 600/424; 600/437; 600/407; 600/443

(58) Field of Classification Search
USPC ......... 600/374, 407, 437, 441, 443, 424, 459, 600/427
See application file for complete search history.

(56) References Cited

U.S. PATENT DOCUMENTS

| | | | |
|---|---|---|---|
| 3,721,227 A | 3/1973 | Larson et al. | |
| 3,968,565 A | 7/1976 | Bertens et al. | |
| 3,983,474 A | 9/1976 | Kuipers | |
| 4,029,084 A | 6/1977 | Soldner | |
| 4,044,273 A | 8/1977 | Kanda et al. | |
| 4,054,881 A | 10/1977 | Raab | |
| 4,108,165 A | 8/1978 | Kopp et al. | |
| 4,249,539 A | 2/1981 | Vilkomerson et al. | |
| 4,289,139 A | 9/1981 | Enjoji et al. | |
| 4,407,294 A | 10/1983 | Vilkomerson | |
| 4,491,137 A | 1/1985 | Jingu | |
| 4,608,989 A | 9/1986 | Drue | |
| 4,635,644 A | 1/1987 | Yagata | |
| 4,671,292 A | 6/1987 | Matzuk | |
| 4,681,103 A | 7/1987 | Boner et al. | |
| 4,742,829 A | 5/1988 | Law et al. | |
| 4,838,506 A | 6/1989 | Cooper | |
| 4,899,756 A | 2/1990 | Sonek | |
| 5,078,144 A | 1/1992 | Sekino et al. | |
| 5,119,818 A | 6/1992 | Carroll et al. | |

(Continued)

FOREIGN PATENT DOCUMENTS

| | | |
|---|---|---|
| DE | 2942405 | 4/1981 |
| EP | 0102800 | 3/1984 |
| EP | 06-17922 A1 | 3/1994 |
| JP | 57-122861 | 7/1982 |

(Continued)

OTHER PUBLICATIONS

Abstract—The SMART needle, Anesthesia, vol. 49, 1994, pp. 889-991.

(Continued)

*Primary Examiner* — Joel Lamprecht
(74) *Attorney, Agent, or Firm* — Dority & Manning, PA

(57) ABSTRACT

Disclosed are medical probe devices and methods for use guiding of percutaneous probes during medical procedures. The probe devices include an ultrasound transducer housing having a passage therethrough configured to accommodate a probe. The devices can be utilized to guide a probe through the probe guide to a percutaneous target with real time visualization of the probe during the procedure. In addition, the devices can include a sterilizable shield including a sterile probe guide such that the transducer housing itself can be separated from a subject by a sterile barrier. The sterilizable shield can be a single-use shield that can prevent contamination and re-use of the shield. The devices can define a beneficial geometry conducive to use by a single operator that can be utilized for percutaneous targets near the skin surface and can enable excellent contact between the device and the skin surface of a subject.

16 Claims, 21 Drawing Sheets

(56) References Cited

U.S. PATENT DOCUMENTS

| | | | |
|---|---|---|---|
| 5,261,409 A | 11/1993 | Dardel | |
| 5,285,154 A | 2/1994 | Burreson | |
| 5,291,090 A | 3/1994 | Dias | |
| 5,329,927 A | 7/1994 | Gardineer et al. | |
| 5,341,810 A | 8/1994 | Dardel | |
| 5,351,004 A | 9/1994 | Daniels | |
| 5,427,108 A | 6/1995 | Bollinger | |
| 5,490,522 A | 2/1996 | Dardel | |
| 5,494,039 A | 2/1996 | Onik et al. | |
| 5,647,373 A | 7/1997 | Paltieli | |
| 5,758,650 A | 6/1998 | Miller et al. | |
| 5,871,448 A | 2/1999 | Ellard | |
| 5,879,297 A | 3/1999 | Haynor et al. | |
| 5,924,992 A | 7/1999 | Park et al. | |
| 5,928,219 A | 7/1999 | Friend et al. | |
| 5,941,889 A | 8/1999 | Cermak | |
| 5,971,949 A | 10/1999 | Levin et al. | |
| 6,017,316 A | 1/2000 | Ritchart et al. | |
| 6,027,457 A | 2/2000 | Shmulewitz et al. | |
| 6,129,668 A | 10/2000 | Haynor et al. | |
| 6,138,495 A | 10/2000 | Paltieli et al. | |
| 6,206,832 B1 | 3/2001 | Downey et al. | |
| 6,216,028 B1 | 4/2001 | Haynor et al. | |
| 6,216,029 B1 | 4/2001 | Paltieli | |
| 6,261,234 B1 | 7/2001 | Lin | |
| 6,263,230 B1 | 7/2001 | Haynor et al. | |
| 6,296,614 B1 | 10/2001 | Pruter | |
| 6,309,304 B1 | 10/2001 | Ondrus | |
| 6,336,899 B1 | 1/2002 | Yamazaki | |
| 6,361,499 B1 | 3/2002 | Bates et al. | |
| 6,379,307 B1 | 4/2002 | Filly et al. | |
| 6,398,711 B1 | 6/2002 | Green et al. | |
| 6,409,686 B1 | 6/2002 | Guthrie et al. | |
| 6,419,653 B2 | 7/2002 | Edwards et al. | |
| 6,443,902 B1 | 9/2002 | Sasady | |
| 6,457,365 B1 | 10/2002 | Stephens et al. | |
| 6,475,152 B1 | 11/2002 | Kelly, Jr. et al. | |
| 6,527,731 B2 | 3/2003 | Weiss et al. | |
| 6,554,771 B1 | 4/2003 | Buil et al. | |
| 6,582,368 B2 | 6/2003 | Holdaway et al. | |
| 6,612,991 B2 | 9/2003 | Sauer et al. | |
| 6,689,067 B2 | 2/2004 | Sauer et al. | |
| 6,690,159 B2 | 2/2004 | Burreson et al. | |
| 6,695,786 B2 | 2/2004 | Wang et al. | |
| 6,755,789 B2 | 6/2004 | Stringer et al. | |
| 6,758,817 B1 | 7/2004 | Pruter et al. | |
| 6,764,449 B2 | 7/2004 | Lee et al. | |
| 6,785,571 B2 | 8/2004 | Glossop | |
| 6,814,704 B2 | 11/2004 | Weilandt | |
| 6,875,179 B2 | 4/2005 | Ferguson et al. | |
| 7,068,867 B2 | 6/2006 | Adoram et al. | |
| 7,241,267 B2 | 7/2007 | Furia | |
| 7,244,234 B2 | 7/2007 | Ridley et al. | |
| 7,351,205 B2 | 4/2008 | Szczech et al. | |
| 7,452,331 B1 | 11/2008 | Pruter | |
| 8,437,833 B2 * | 5/2013 | Silverstein | 600/427 |
| 2001/0031941 A1 | 10/2001 | Edwards et al. | |
| 2002/0007119 A1 | 1/2002 | Pelissier | |
| 2002/0082518 A1 | 6/2002 | Weiss et al. | |
| 2002/0123689 A1 | 9/2002 | Furia | |
| 2002/0156376 A1 | 10/2002 | Wang et al. | |
| 2002/0173719 A1 | 11/2002 | Zhao et al. | |
| 2002/0183740 A1 | 12/2002 | Edwards et al. | |
| 2003/0016006 A1 | 1/2003 | Khalfin | |
| 2003/0036709 A1 | 2/2003 | Jordan, III | |
| 2003/0078502 A1 | 4/2003 | Miyaki et al. | |
| 2003/0097066 A1 | 5/2003 | Shelby et al. | |
| 2003/0100814 A1 | 5/2003 | Kindlein | |
| 2003/0120154 A1 | 6/2003 | Sauer et al. | |
| 2003/0120155 A1 | 6/2003 | Sauer et al. | |
| 2003/0149366 A1 * | 8/2003 | Stringer et al. | 600/464 |
| 2003/0163142 A1 | 8/2003 | Paltieli et al. | |
| 2003/0171681 A1 | 9/2003 | Weilandt | |
| 2003/0233046 A1 | 12/2003 | Ferguson et al. | |
| 2004/0034297 A1 | 2/2004 | Darrow et al. | |
| 2004/0097805 A1 | 5/2004 | Verard et al. | |
| 2004/0122314 A1 | 6/2004 | Fattah et al. | |
| 2004/0131299 A1 | 7/2004 | Adoram et al. | |
| 2004/0133111 A1 | 7/2004 | Szczech et al. | |
| 2004/0133168 A1 | 7/2004 | Salcudean et al. | |
| 2004/0143252 A1 | 7/2004 | Hurst | |
| 2004/0193047 A1 | 9/2004 | Pelissier et al. | |
| 2004/0250819 A1 | 12/2004 | Blair et al. | |
| 2004/0260174 A1 | 12/2004 | Keene | |
| 2005/0033315 A1 | 2/2005 | Hankins | |
| 2005/0101868 A1 | 5/2005 | Ridley et al. | |
| 2005/0234476 A1 | 10/2005 | Whitmore, III et al. | |
| 2005/0272974 A1 | 12/2005 | Iddan | |
| 2007/0038113 A1 | 2/2007 | Oonuki et al. | |
| 2007/0073155 A1 | 3/2007 | Park et al. | |
| 2007/0078334 A1 | 4/2007 | Scully et al. | |
| 2007/0078346 A1 | 4/2007 | Park et al. | |
| 2007/0149878 A1 | 6/2007 | Hankins | |
| 2007/0208255 A1 | 9/2007 | Ridley et al. | |
| 2008/0064960 A1 | 3/2008 | Whitmore, III et al. | |
| 2008/0071215 A1 | 3/2008 | Woods et al. | |
| 2008/0214925 A1 | 9/2008 | Wilson et al. | |
| 2008/0255475 A1 | 10/2008 | Kondrosky et al. | |
| 2009/0143684 A1 | 6/2009 | Cermak et al. | |
| 2009/0156926 A1 | 6/2009 | Messerly et al. | |
| 2009/0234328 A1 | 9/2009 | Cox et al. | |
| 2010/0036227 A1 | 2/2010 | Cox et al. | |
| 2010/0191224 A1 | 7/2010 | Butcher | |
| 2010/0204569 A1 | 8/2010 | Burnside et al. | |
| 2011/0015533 A1 | 1/2011 | Cox et al. | |
| 2011/0196248 A1 | 8/2011 | Grunwald | |
| 2011/0282188 A1 | 11/2011 | Burnside et al. | |
| 2011/0295108 A1 | 12/2011 | Cox et al. | |
| 2012/0059270 A1 | 3/2012 | Grunwald | |
| 2012/0095319 A1 | 4/2012 | Krondrosky et al. | |
| 2012/0143029 A1 | 6/2012 | Silverstein et al. | |
| 2012/0157849 A1 | 6/2012 | Ridley et al. | |
| 2012/0157855 A1 | 6/2012 | Ridley et al. | |
| 2012/0220854 A1 | 8/2012 | Messerly et al. | |

FOREIGN PATENT DOCUMENTS

| | | |
|---|---|---|
| JP | 59-007919 | 1/1984 |
| JP | 06-205776 | 7/1994 |
| JP | 08-000614 | 1/1996 |
| JP | 08-229042 | 9/1996 |
| JP | 10057376 | 3/1998 |
| JP | 2002-112998 | 4/2002 |
| JP | 2003-334191 | 11/2003 |
| JP | 09-322880 | 12/2007 |
| WO | WO 84/03034 | 8/1984 |
| WO | WO 97/03609 | 2/1997 |
| WO | WO 00/40155 | 7/2000 |
| WO | WO 00/57767 | 10/2000 |
| WO | WO 00/63658 | 10/2000 |
| WO | WO 2005/009509 | 2/2005 |
| WO | WO 2005/046444 | 5/2005 |

OTHER PUBLICATIONS

Product Information from Hitachi, Probes and Systems, 5 pages, 2003.
Product Information Sheet for Biopsy Probe EUP-B31 from Hitachi, www.hitachimed.com, Sep. 22, 2003.
Product Information Sheet on Probe Covers & Surgical Drapes from Protek Medical Products, Inc., 2 pages, 2004.
JP App. No. 2006539726 Office Action dated Jun. 1, 2010.
JP App. No. 2006539726 Office Action dated Sep. 28, 2010.
EP Search Report PCT/US2004037268, Oct. 31, 2007.
International Search Report for PCT/US2010/046751, Dec. 10, 2010.
International Search Report for PCT/US2010/046756, Jan. 13, 2011.
Evidence Report/Technology Assessment, No. 43, *Making Health Care Safer: A Critical Analysis of Patient Safety Practices*, University of California at San Francisco (UCSF)—Stanford University, Jul. 20, 2001, 25 pages.
Product Data from Ascension Technology Corporation—3D Guidance medSAFE™, Jan. 2009, 3 pages.

(56) References Cited

OTHER PUBLICATIONS

Product Information for Civco Medical Solutions and Ascension Technology Corporation, Nov. 26, 2008, 8 pages.

Related U.S. Patent Application Form, Mar. 10, 2010.

European search report dated Feb. 10, 2014 for European Application No. 13152351.

* cited by examiner

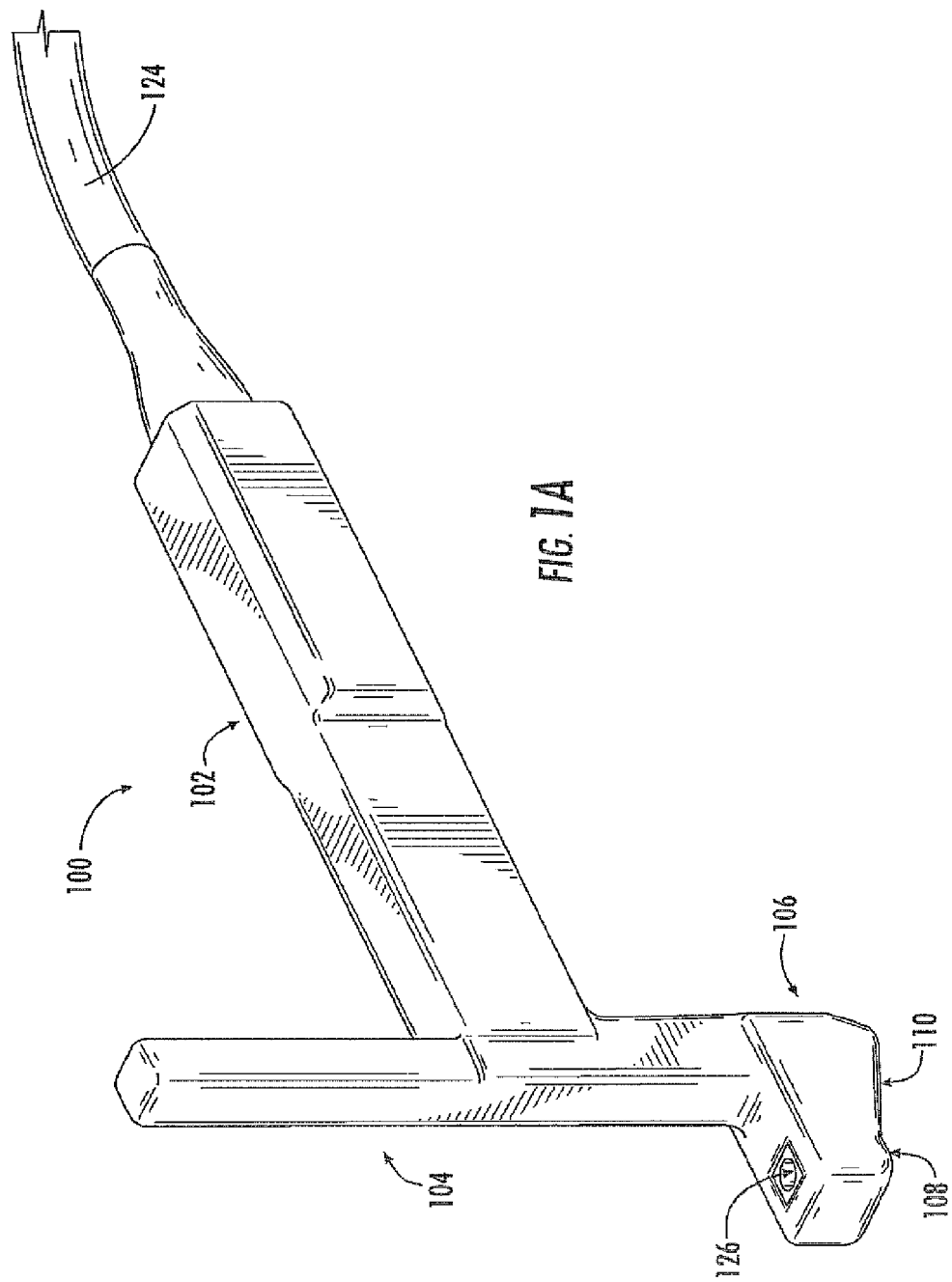

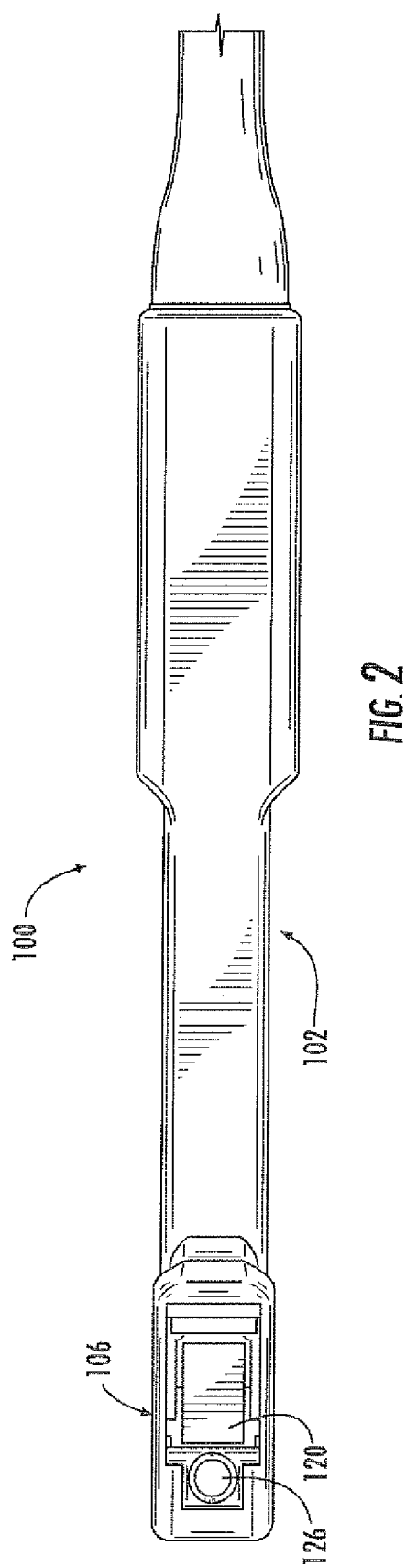

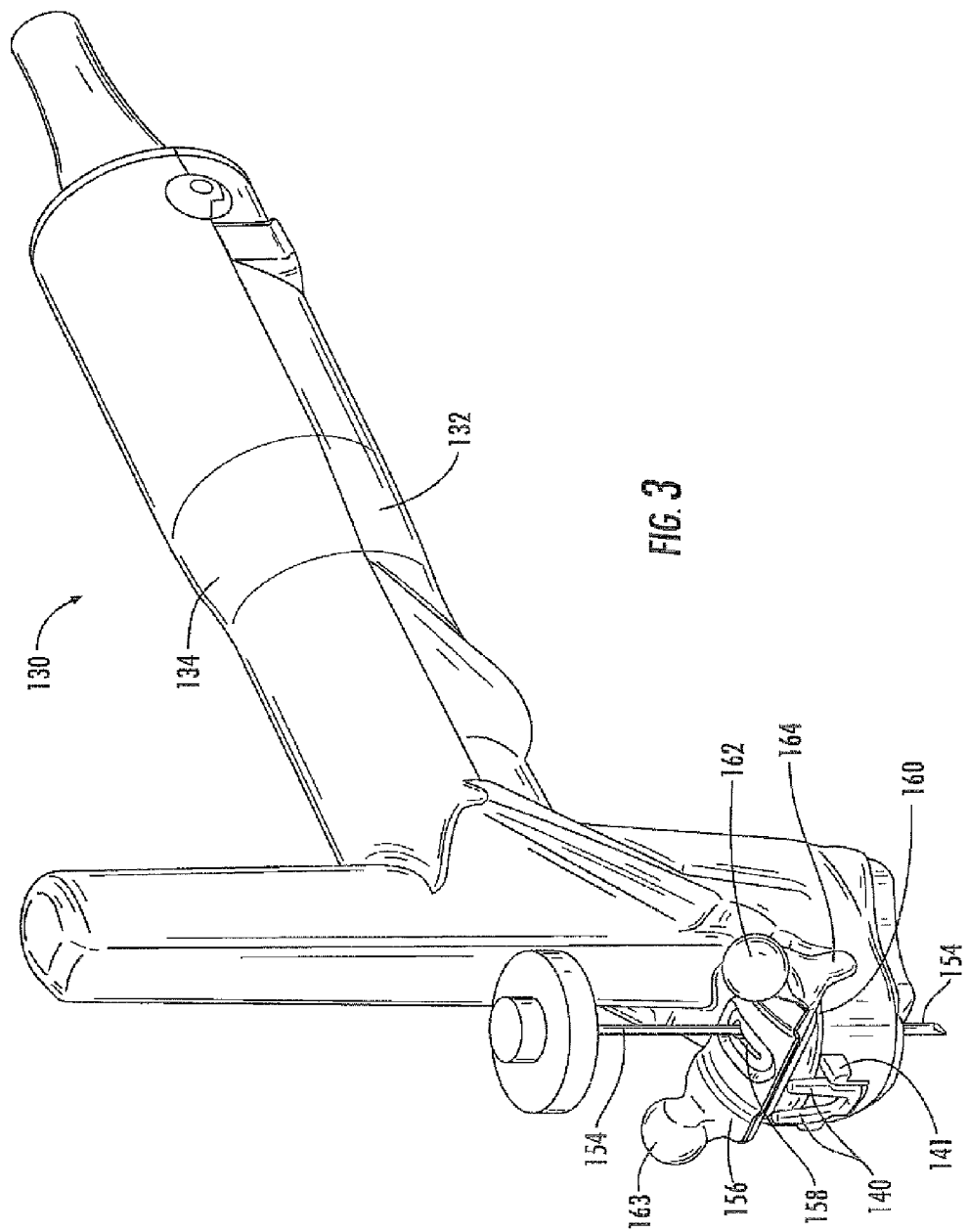

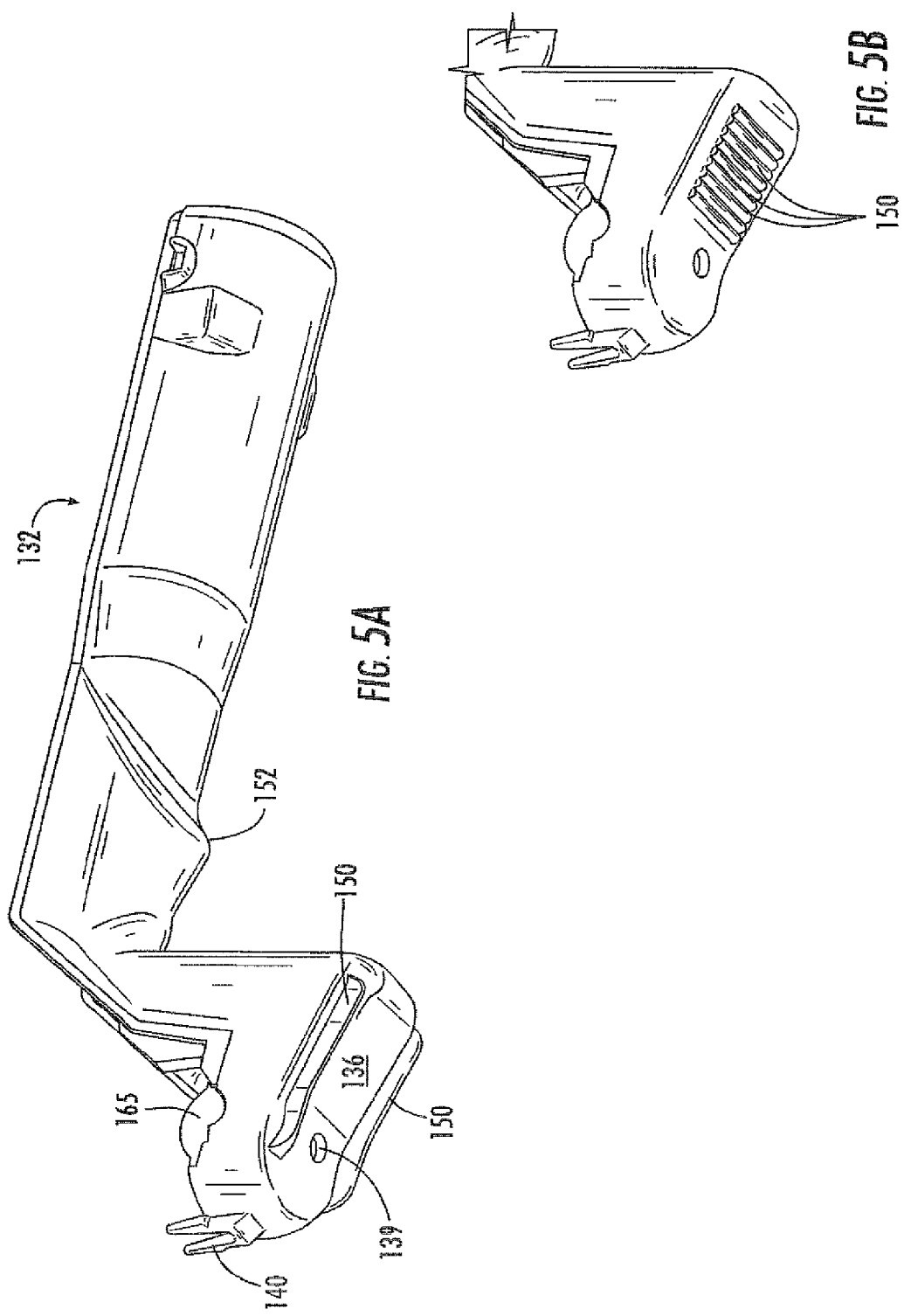

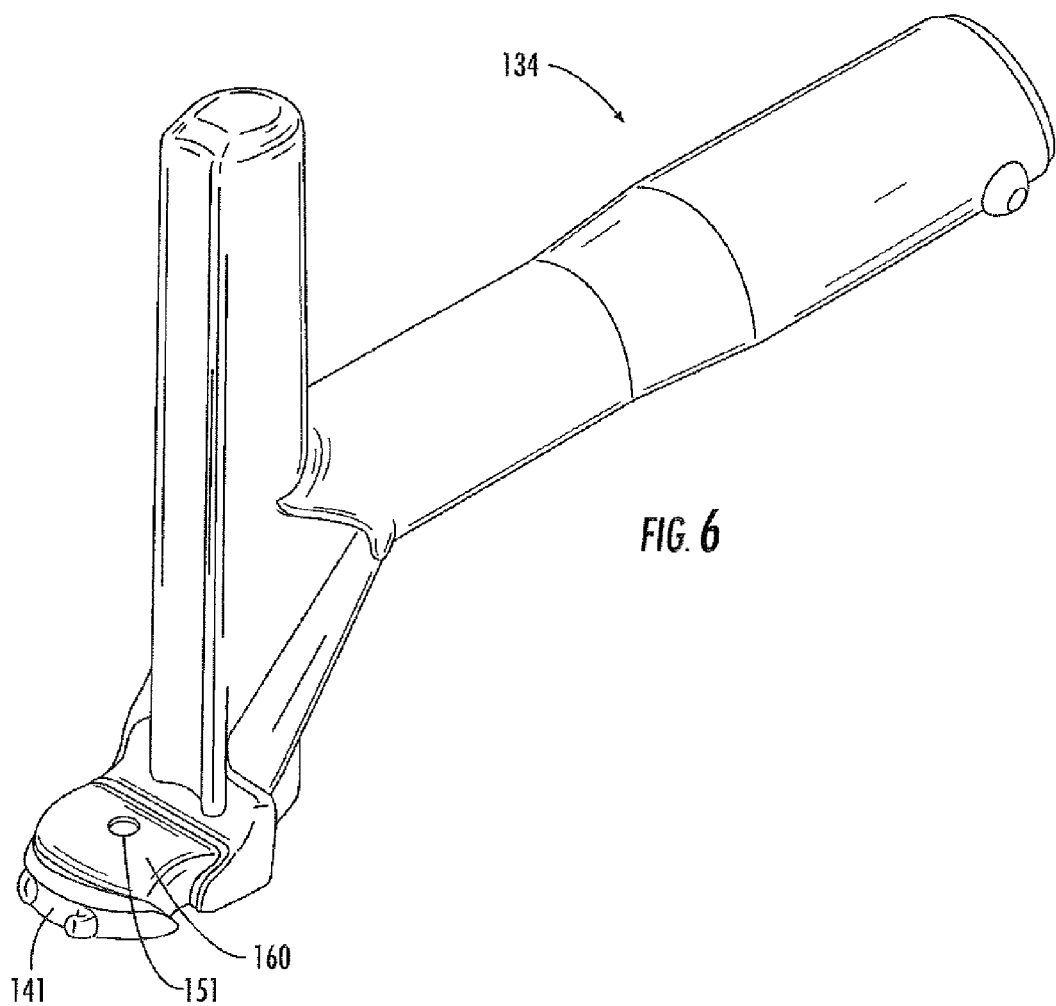

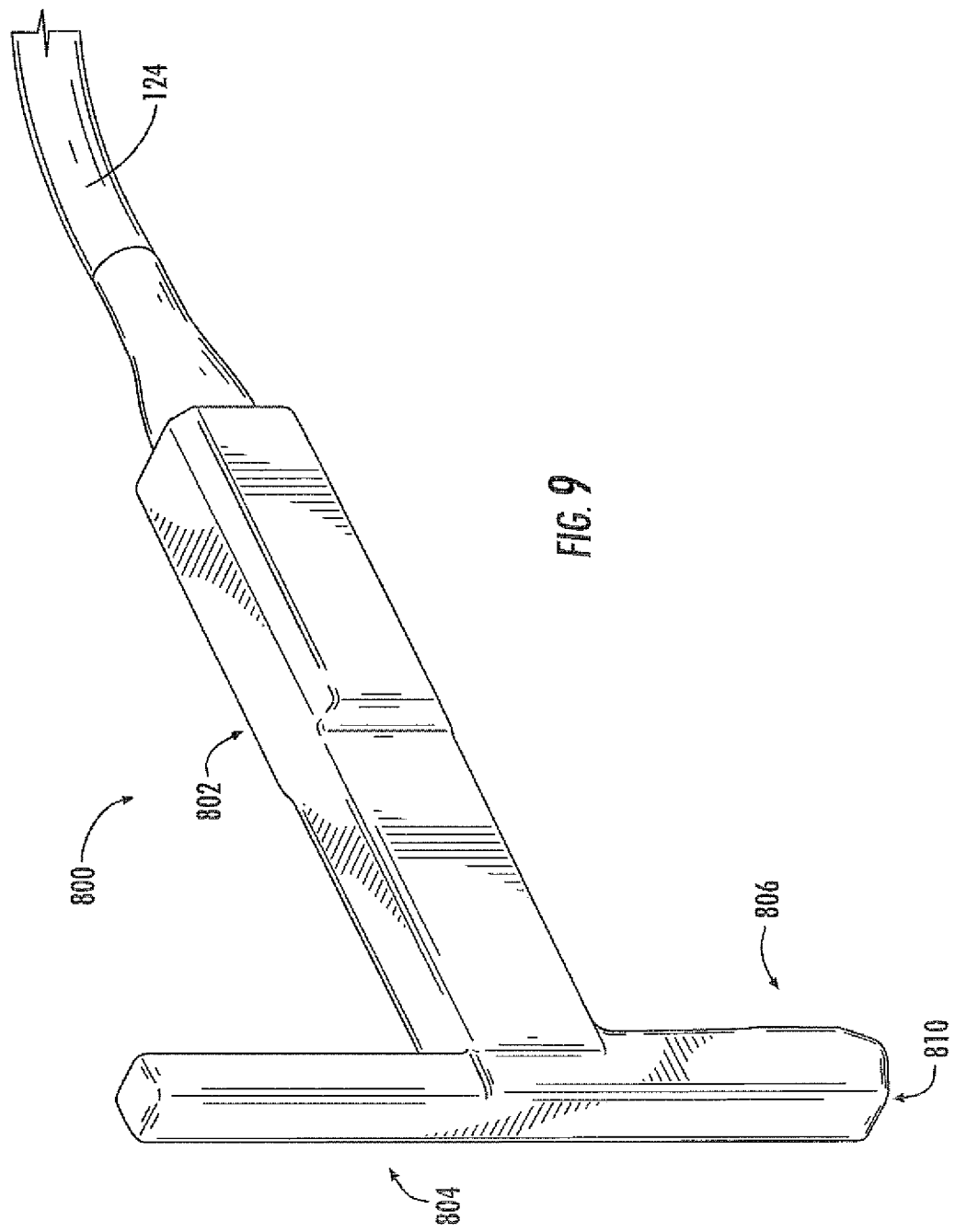

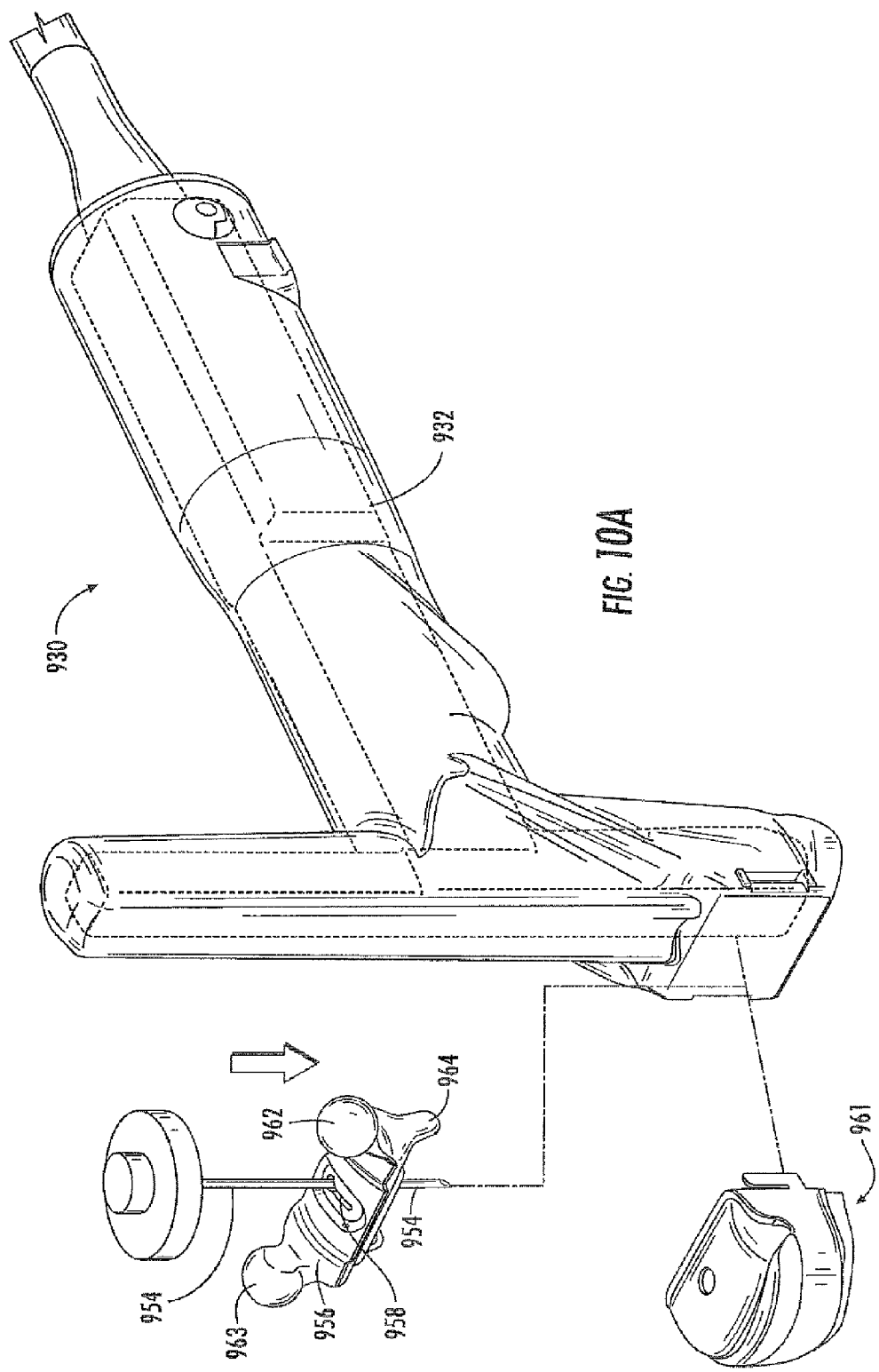

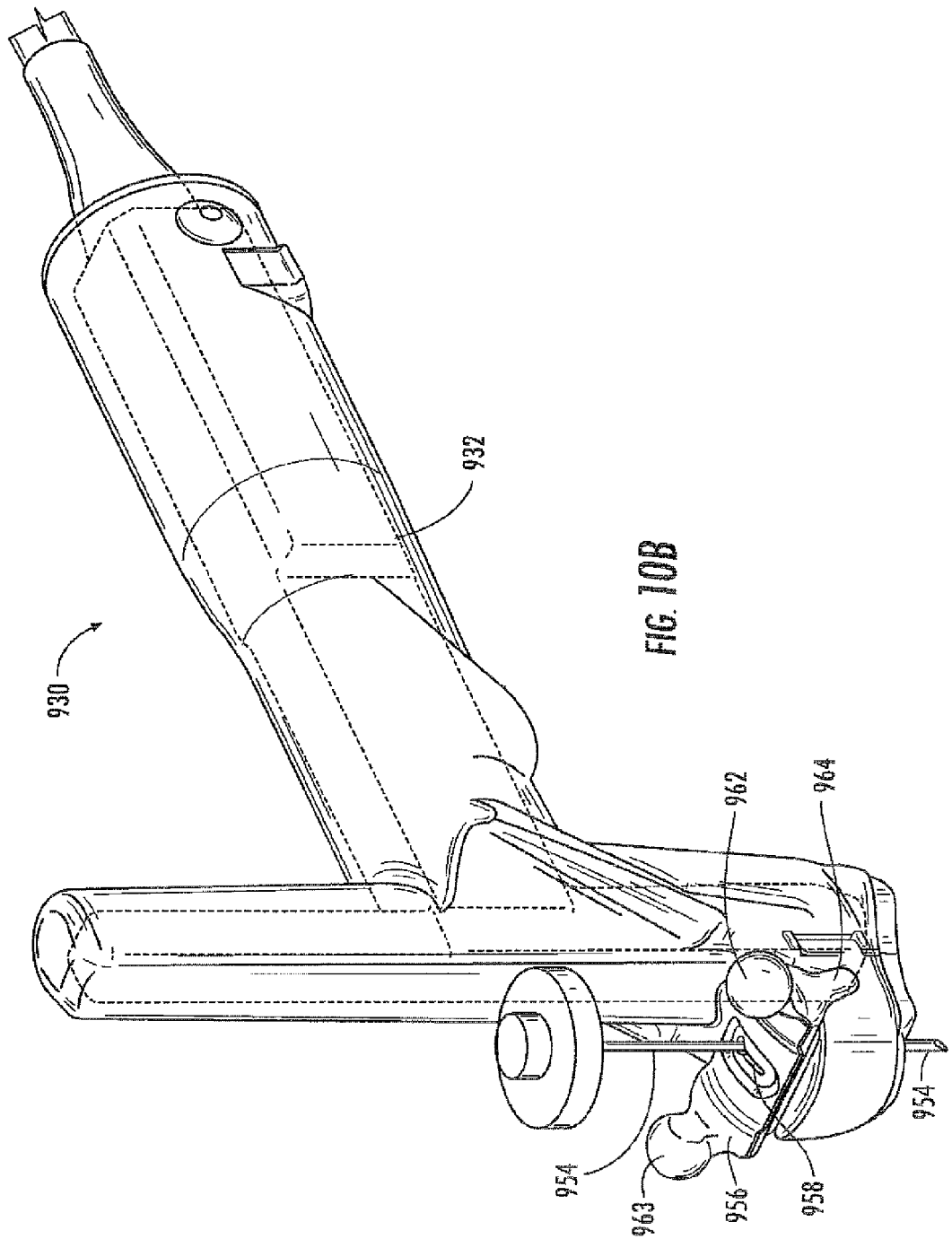

ULTRASOUND GUIDED PROBE DEVICE AND STERILIZABLE SHIELD FOR SAME

BACKGROUND OF THE INVENTION

Medical probe devices are utilized for many purposes, chief of which include catheterization, centesis, and biopsy procedures. Percutaneous placement of probes using these devices is often performed with techniques which rely on ascertaining the correct locations of palpable or visible structures. This is neither a simple nor a risk-free procedure. For instance, proper insertion and placement of a percutaneous probe depends on correct localization of anatomical landmarks, proper positioning of the patient in relation to the care provider, and awareness of both the target's depth and angle from the point of probe insertion. Risks of unsuccessful placement of a probe can range from minor complications, such as patient anxiety and discomfort due to repetition of the procedure following incorrect initial placement, to severe complications, such as pneumothorax, arterial or venous laceration, or delay of delivery of life-saving fluids or medications in an emergency situation.

Ultrasound guided techniques and devices have been developed to aid in correct placement of percutaneous probes. Ultrasound guided techniques often utilize two people, an ultrasound operator who locates the internal target and keeps an image of the target centrally located on a monitor, and a care provider who attempts to guide the probe to the target based upon the sonogram. Such techniques are very difficult perceptually. For instance, these techniques are complicated by the fact that the person targeting the tissue with the probe is not the same person as is operating the ultrasound. In addition, the generally thin, cylindrical probe is usually small and reflects very little of the ultrasound beam. Moreover, as the cylindrical probe and the ultrasound beam are not generally normal to one another, the small amount of ultrasonic energy that is reflected from the probe will reflect at an angle to the incident beam, resulting in little if any of the reflected energy being detected by the ultrasound transducer. As a result, the probe itself is difficult to visualize in the sonogram and the person placing the probe must attempt to guide the probe to the correct location using minimal visual feedback. For example, the only visual feedback available is often only subtle artifacts of the motion of the probe such as slight changes in the sonogram as the probe deflects and penetrates the surrounding tissue. The trained observer can pick up subtle ultrasonic shadow artifacts deep to the probe created when the probe blocks the transmission of the ultrasound beam to the tissue below, and such subtle artifacts can be used to help guide the probe to the targeted location.

In an attempt to relieve the difficulties of ultrasound guided probe techniques, systems have been developed including a probe guide which can be attached to an ultrasound transducer housing. Problems still exist with such devices however. For instance, the probe guide is to one side of the ultrasound transducer housing in these devices, and the probe is often inserted at a fixed angle to the scanned plane displayed on the sonogram, restricting the intersection of the scanned plane and the point of the probe to a very small area in space. In addition, and as with hand-guided ultrasound techniques, very little, if any, ultrasonic energy is reflected from the probe back to the transducer. In fact, due to the lack of lateral motion of the probe, visual cues to the location of the probe tip may be even more difficult to discern on a sonogram when using these devices. In addition, in many of these devices, the probe passes through the ultrasound beam at a fixed depth range depending on the set angle of the probe guide, and this may not correspond to the depth of the target, in which case it may not be possible to show the juncture of the target and the probe tip on the sonogram at all.

What are needed in the art are improved ultrasound devices and methods for using such devices. For instance, what are needed in the art are ultrasound probe devices that can be utilized by a single operator to accurately visualize the delivery of a probe to a percutaneous target.

SUMMARY OF THE INVENTION

Disclosed in one embodiment is a medical probe device. The skin contacting surface can include a first portion and a second portion that are angled with respect to one another. More specifically, the first portion can define a first plane and the second portion can define a second plane, and these two planes can intersect one another to define an angle therebetween that is greater than about 150° and less than 180°. In addition, the first portion of the skin contacting surface can define a probe guide therethrough, and the second portion can be associated with an ultrasound transducer such that an ultrasonic beam transmitted from the ultrasound transducer issues from the second portion. In one embodiment, the first portion of the skin contacting surface can be defined by a first portion of the medical probe device and the second portion of the skin contacting surface can be defined by a second portion of the medical probe device, and the first and second portions of the medical probe device can be removably cooperable with one another.

The probe device can be an ultrasound transducer housing, or, in another embodiment, can include a sterilizable shield that can enclose an ultrasound transducer housing.

A probe device as disclosed herein can also include a clamp for clamping a probe in the probe guide of the device, for instance after the probe tip has reached a targeted percutaneous target.

Disclosed devices can be connectable to a monitor for displaying a sonogram. Moreover, the path of a probe guided through the probe guide can define a line that is coincident (i.e., within) the scanned plane of a sonogram formed by the ultrasound device.

A device can include a detector for detecting motion of a probe within the probe guide. Information from the detector can be processed and, in one embodiment, can be displayed as an image of a virtual probe on the monitor overlaying the sonogram, providing a real-time visualization of the location of the probe tip during a procedure.

A probe device can include additional beneficial features. For example, in one embodiment, a skin contacting surface of a probe device can include at least one raised ridge on the surface that can improve coupling between the skin and the probe device, generally in conjunction with ultrasonic gel between the two. In another embodiment, a skin contacting surface can include a wedge formed of an ultrasonic transmissive material to improve coupling between the skin and the probe device and/or to improve visualization of percutaneous targets that are close to the surface of the skin.

Also disclosed herein is a single-use sterilizable shield as can be utilized with an ultrasound transducer. In one embodiment, a sterilizable shield can include a first section, a second section and a fastener for connecting the first section and the second section to one another. Beneficially, the fastener can be a single-use fastener that can be permanently disabled upon disconnection and separation of the first section and the second section from one another that can prevent reuse of a shield and enhance patient safety.

Also disclosed is a multi-piece device including multiple removably attachable portions. For instance, a device can include a first portion that incorporates an ultrasound transducer and a second portion that defines all or a portion of a probe guide, and the two portions can be removably attached to one another. A device can also include a detector for detecting the presence or the motion of a probe within the probe guide.

Also disclosed are methods for guiding a probe to a percutaneous target. Methods can include, for example, utilizing a probe guide including an ultrasound device with a single-use sterilizable shield and disabling the shield upon disassembly of the device. Beneficially, disclosed methods can be carried out by a single operator during a medical procedure.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1A illustrates one embodiment of an ultrasound device as disclosed herein;

FIG. 2 illustrates a bottom view of the device of FIG. 1;

FIG. 3 illustrates one embodiment of a multi-section sterilizable shield as disclosed herein;

FIG. 5A illustrates a bottom view of the lower section of the sterilizable shield illustrated in FIG. 3;

FIG. 5B illustrates a partial bottom view of another embodiment of a sterilizable shield as disclosed herein;

FIG. 6 illustrates the upper section of the sterilizable shield illustrated in FIG. 3;

FIG. 9 illustrates an ultrasound transducer housing that can be removably attachable to a portion of a probe device defining a probe guide;

FIGS. 10A and 10B illustrate a probe device including the ultrasound transducer housing of FIG. 9 enclosed in a sterilizable shield portion, a separable portion removably attachable thereto that defines a probe guide, and a clamp removably attachable thereto, with FIG. 10A showing the sections removed from one another and FIG. 10B showing the sections when attached together.

Figure 1B:
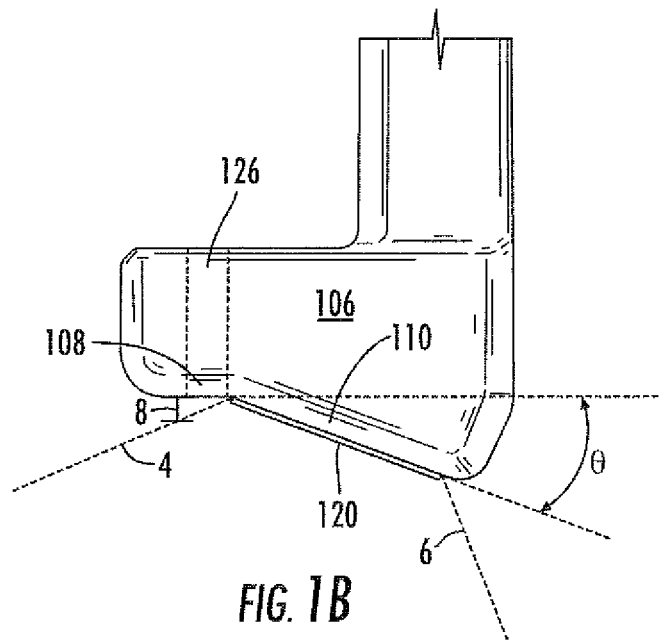
FIG. 1B illustrates a side view of the base of the device of FIG. 1A.

Repeat use of reference characters in the present specification and drawings is intended to represent the same or analogous features of elements of the disclosed subject matter. Other objects, features and aspects of the subject matter are disclosed in or are obvious from the following detailed description.

DETAILED DESCRIPTION OF PREFERRED EMBODIMENTS

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

Definitions

As utilized herein, the term "probe" generally refers to a device that can be guided to a percutaneous location, for instance for delivery of a therapeutic, e.g., a compound or a treatment, to the location; for removal of material from the location; and so forth. For example, the term "probe" can refer to a needle, a tube, a biopsy device, or any other item that can be guided to a percutaneous location. In general, a probe can be guided by and used in conjunction with an ultrasound device as described herein.

As utilized herein, the term "probe device" generally refers to a device that can be utilized in conjunction with a probe, but does not necessarily include the probe itself.

Detailed Description

According to one embodiment, disclosed herein are devices and methods for use in guiding a percutaneous probe during a medical procedure. In one preferred embodiment, disclosed herein are probe devices that can include an ultrasound transducer therein. Devices can define an opening to accommodate a probe therethrough so as to improve coordination between a sonogram formed by the ultrasound device and the path of a probe passing through the opening. In one embodiment, disclosed devices can include a visualization system so as to provide a real-time image of a virtual probe on a sonogram and improve delivery of a probe to a percutaneous target.

Also disclosed herein are sterilizable shields that can surround all or a portion of an ultrasound transducer to form a sterilizable probe device. Thus, disclosed probe devices can be utilized in an ultrasound guided medical procedure that requires a sterile field to ensure the safety of a patient. For instance, disclosed devices can be used in a central venous catheterization procedure, in a biopsy procedure, and the like.

Beneficially, disclosed devices can be formed so as to conveniently be utilized by a single operator who can control an ultrasound transducer and also deliver a probe using the probe guidance system. Disclosed devices can include a variety of other beneficial features as well. For example, features of disclosed devices can improve contact and gel coupling between a skin surface and the surface of a device, can improve the effective field of the sonogram formed with the ultrasound transducer, and can prevent non-sterile use of a sterilizable shield of a device, all of which are described in greater detail herein.

In one preferred embodiment, disclosed devices can incorporate a system that can be used to visualize a percutaneous probe as it is being guided with a device. One preferred embodiment of a visualization system as may be incorporated with disclosed devices has been described in U.S. Pat. No. 7,244,234 to Ridley, et al., which is incorporated herein by reference. Through utilization of a visualization system, the path of a probe guided with a device and hence the location of the probe tip can be more clearly known in relation to a target imaged by the ultrasound device.

In accord with the present disclosure, FIG. 1A illustrates one embodiment of an ultrasound transducer housing generally 100. Transducer housing 100 includes handle 102, post 104, and base 106. FIG. 2 provides a bottom view of the transducer housing 100. An ultrasound transducer 120 that transmits and receives ultrasonic waves can be located in base 106, as shown. Ultrasound transducer housing 100 can be formed of any suitable materials. For instance, any moldable polymeric material that can securely encase the ultrasound transducer 120 as well as contain associated electronics, wiring, switches, and the like and will not interfere with the functioning of the transducer 120 can be utilized.

Any type of ultrasound transducer as is generally known in the art can be incorporated in transducer housing 100. By way of example, a piezoelectric transducer formed of one or more piezoelectric crystalline materials arranged in a two or three-dimensional array can be utilized. Such materials generally include ferroelectric piezoceramic crystalline materials such as lead zirconate titanate (PZT). In one embodiment, the elements that form the array can be individual electrode or electrode segments mounted on a single piezoelectric substrate, such as those described in U.S. Pat. No. 5,291,090 to Dias, which is incorporated herein by reference thereto.

In general, an ultrasound transducer 120 can be formed of multiple elements; however, single crystal devices are also encompassed by the present disclosure. The use of a multiple element ultrasound transducer can be advantageous in certain embodiments, as the individual elements that make up the array can be controlled so as to limit or prevent any break or edge effects in the sonogram. For instance, the firing sequence of individual crystals can be manipulated through various control systems and prevent any possible 'blind spots' in the sonogram as well as to clarify the edges of individual biological structures in the sonogram. Such control systems are generally known in the art and thus will not be described in detail.

Referring again to FIG. 1A, ultrasound transducer housing 100 defines a probe guide opening 126 that passes through base 106. As can be seen in FIG. 2, probe guide opening 126 can be aligned with transducer 120. A probe that is guided through the probe guide opening 126 can travel on a path that is generally parallel to the scanned plane of a sonogram formed by use of the ultrasound device. In general, the scanned plane (i.e., the plane of the sonogram) is the geometric central plane of the beam transmitted from the ultrasound transducer 120. In one preferred embodiment, the path of a probe guided through probe guide opening 126 can be within the scanned plane. This is not a requirement of the present disclosure, however. For instance, the path of a probe passing through probe guide opening 126 can be at an angle to the scanned plane such that it intersects the scanned plane at a point. By way of example, the line defined by the path of a probe passing through the probe guide opening 126 can be at an angle of ±1° of the scanned plane, or at a greater angle, in another embodiment. For instance, a line defined by the path of a probe passing through the probe guide opening 126 can be at an angle of ±10, °±20°, ±45°, or even greater, in other embodiments.

Generally, ultrasound transducer 120 can be connected via signal wires in a cable 124 that leads to a processor that processes the data to form a sonogram on a monitor, as is generally known in the art. In the particular embodiment as illustrated in FIG. 1A, cable 124 is internal to handle 102 of the ultrasound transducer housing 100, though this particular arrangement is not a requirement of the disclosure. Handle 102 can generally be set at an angle to post 104 of transducer housing 100 so as to be comfortably held in the hand while the device is being utilized. For instance, in the illustrated embodiment, handle 102 is about 90° to post 104, though this angle can be varied as desired. Moreover, in another embodiment described further herein, a device need not include an extending handle portion at all.

Referring to FIG. 1B, base 106 defines a lower surface 108 defining probe guide opening 126 and lower surface 110 from which an ultrasonic beam emitted by transducer 120 can issue. Surfaces 108 and 110 together can form a skin contacting surface on the base 106 of the device 100. As can be seen, surfaces 108 and 110 are contiguous and angled with respect to one another. The angle between surface 108 and 110 can vary. For instance, in one embodiment the angle marked as θ in FIG. 1B can vary from 0 to about 30° or from about 10° to about 20° in another embodiment. Accordingly, the angle between surfaces 108 and 110 can be greater than about 150° and less than 180° in one embodiment, or greater than about 160° and less than about 170° in another embodiment.

It has been found that such geometry can be beneficial in certain embodiments. For instance, referring to FIG. 1B, base 106 is illustrated with the edges of a scanned plane formed by ultrasound transducer 120 shown within broken lines 4 and 6. The distance 8 from the termination of probe guide opening 126 to the edge 4 of the scanned plane is also shown. During use, the portion of base 106 including surface 110 can press into the skin of a subject somewhat and ensure good contact between the ultrasound transducer 120, ultrasonic gel, and the skin. Upon passing a probe through the probe guide opening 26, the probe will contact the skin and travel the short percutaneous distance 8 before entering the ultrasound beam. The distance 8 can depend upon the angle between the surfaces 108 and 110, but can be relatively small. For instance, distance 8 can be less than about 25 mm, less than about 10 mm, less than about 5 mm or less than about 1 mm.

Figure 1C:
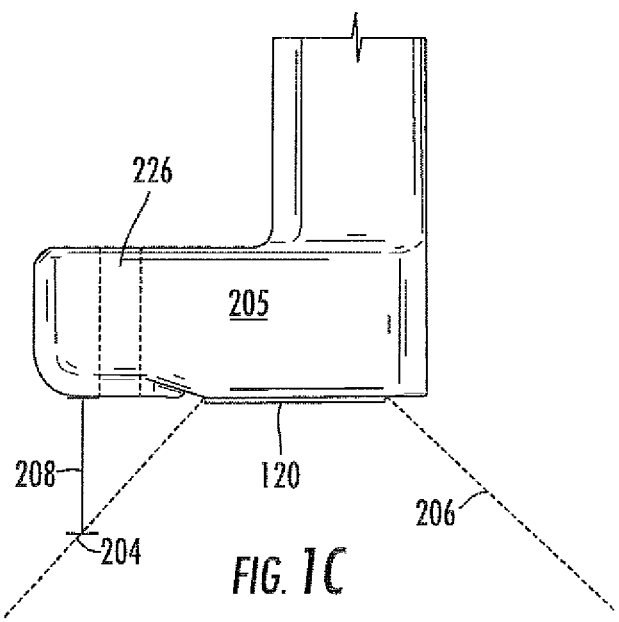
FIG. 1C illustrates a side view of the base of another embodiment of an ultrasound device as disclosed herein.

In comparison, FIG. 1C illustrates a base 205 in which the entire bottom edge of base 205 is planar, i.e., the skin contacting surface of base 205 does not include angled portions. FIG. 1C also illustrates the edges of a scanned plane formed by transducer 120 by use of broken lines 204 and 206. As can be seen, the distance 208 between the point a probe will exit probe guide opening 226 and enter the scanned plane at 204 is greater than the distance 8 in the embodiment in FIG. 1B. An embodiment including a base that defines an angled bottom surface, as is illustrated in FIG. 1B may be preferred in those embodiments in which a percutaneous target may be close to the skin surface.

It should also be understood that while the skin contacting surface and portions thereof of the illustrated probe devices are generally planar, this is not a requirement of the disclosed subject matter. For instance, with regard to FIG. 1B, surface 108 and/or surface 110 can be curved, e.g., can define an arcuate profile along either or both of the axes of the surface. In this embodiment, a curved surface can define a plane between the intersection line of two portions (e.g., surface 108 and surface 110) forming the skin contacting surface and a point at the outer edge of the curved surface. Planes defined by a curved skin contacting surface can correspond in a like manner to a planar skin contacting surface (or portions thereof) as described above.

In another embodiment, the skin contacting surface of a device can be associated with a removably cooperable material so as to encourage improved imaging of a percutaneous location. For instance, a planar skin contacting surface, such as is illustrated in FIG. 1C, or a portion of an angled skin contacting surface, such as surface 108 of FIG. 1B, can be associated with an ultrasound transmissive wedge formed of an ultrasonic transmissive material so as to alter the relative orientation between the skin surface and an ultrasound device. For instance a pliable saline-filled container can be held against or attached to the base of surface 108 to alter the relative orientation of the surfaces. Such a device can be utilized to, e.g., more clearly visualize percutaneous targets that are close to the skin surface. An ultrasound transmissive wedge can be located on the skin contacting surface of a device utilizing a small amount of ultrasonic gel for a temporary attachment, or utilizing a biocompatible adhesive for a more permanent attachment, or by any other suitable adherence method.

It should be understood that any particular geometric configuration for transducer housing 100 and its individual sections is not essential to the present invention. For example, the base 106 of transducer housing 100 may be oblong, square, round, rectangular or any other suitable shape. In certain embodiments, the shape of ultrasound housing 100 may be particularly designed to fit specific locations of the anatomy. For example, ultrasound housing 100 may be shaped to be utilized specifically for infraclavicular approach to the subclavian vein, approach to the internal jugular vein, specific biopsy procedures including, without limitation, breast biopsy, thyroid nodule biopsy, prostate biopsy, lymph node biopsy, and so forth, or some other specific use. Variations in shape for any particular application can include, for example, a specific geometry for the footprint of base 106, alteration in the size of post 104 and/or handle 102, as well as variation in angles at which various elements of a device meet each other, such as the angle defined by the bottom of base 106 previously discussed. For example, the footprint of base 106 can be any suitable shape and size, e.g., rectangular, round, oblong, triangular, etc. By way of example, the skin contacting surface of base 106 can be between about 0.5 inches and about 6 inches on its greatest length. In one embodiment, the footprint of base 106 can be about 0.5 inches on its greatest width so as to promote stability of the device during use. In other embodiments, it can be larger, however, such as about 1 inch on its greatest width, about 2 inches on its greatest width, or even larger.

Transducer housing 100 can be used as is, with no additional shield or covering over the housing 100. According to this embodiment, a probe, e.g., a needle, can pass through probe guide opening 126 and can be directed to a target that is visualized on a sonogram formed by use of ultrasound transducer 120. According to another embodiment, however, all or a portion of transducer housing 100 can be encased in a sterilizable shield, for instance in those embodiments in which a probe is intended for use in a sterile field. According to this embodiment, a transducer housing can be encased in a sterilizable shield that can provide a sterile barrier between a patient and the ultrasound transducer housing 100 during a medical procedure.

A sterilizable shield can generally be formed of a number of different sterilizable, biocompatible materials. For instance, a sterilizable shield can be formed of relatively inexpensive single-use materials that can be sterilized as are generally known in the art such that the entire shield can be properly disposed of following use. In another embodiment, a sterilizable shield can be utilized multiple times, in which case it can be formed of a material that can be properly sterilized between uses. By way of example, a sterilizable shield can be formed of a moldable or extrudable thermoplastic or thermoset polymeric material including, without limitation, polyethylene, polypropylene, polymethylpentene (TPX), polyester, polyvinyl chloride, polycarbonate, polystyrene, and so forth.

FIG. 3 illustrates one example of a sterilizable shield 130 as may be utilized to encase ultrasound transducer housing 100. Sterilizable shield 130 can include a lower section 132, details of various embodiments of which are shown in FIG. 4 and FIG. 5, and an upper section 134, details of which are shown in FIG. 6.

Figure 4:
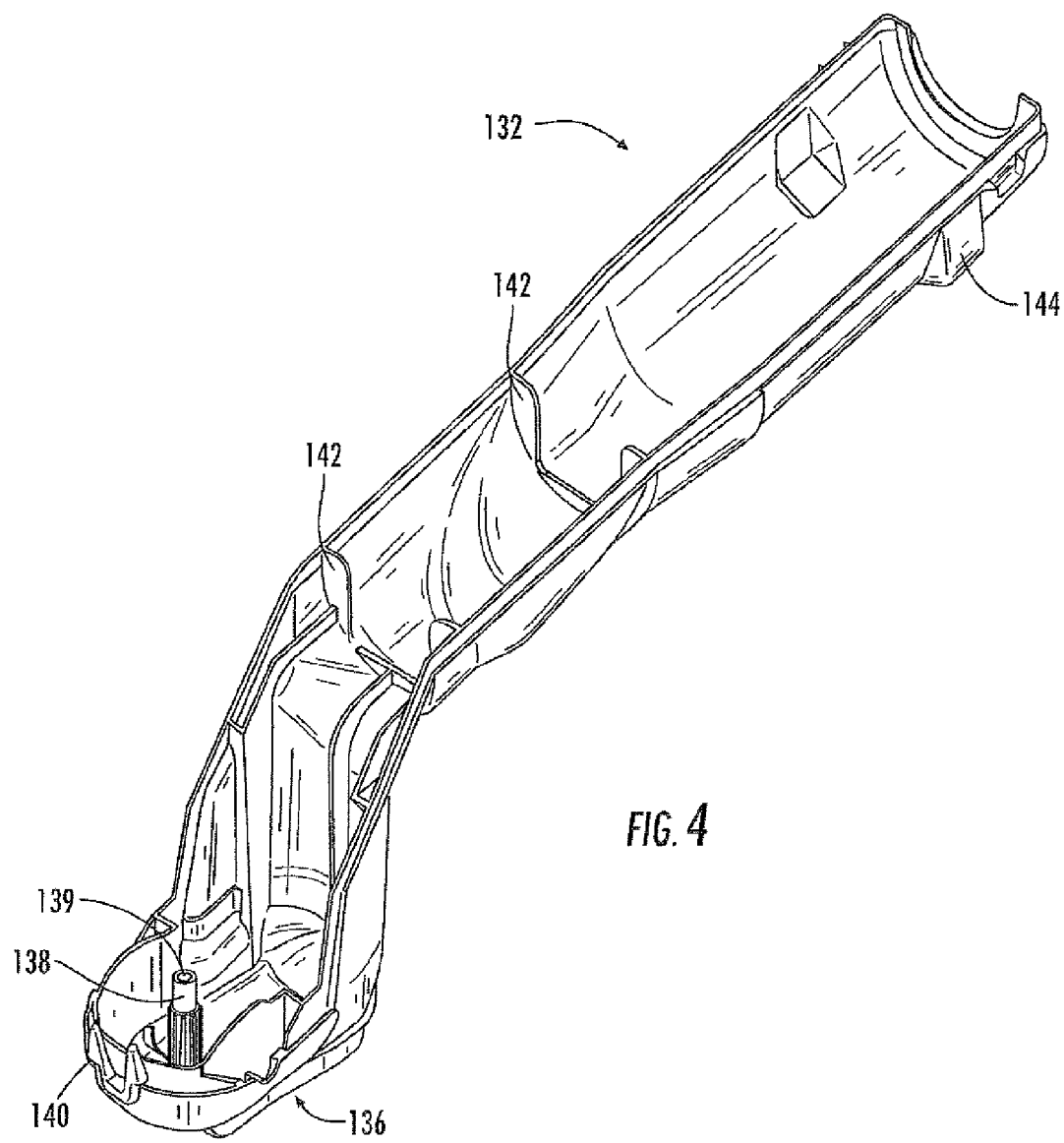
FIG. 4 illustrates the lower section of the sterilizable shield illustrated in FIG. 3.

With reference to FIG. 4, shield section 132 can include a base 136 formed of an ultrasonic transmissive material. Base 136 can be of any suitable size and shape, but formed such that ultrasound transducer housing base 106 may be seated firmly in shield base 136. Generally, a small amount of an ultrasonic gel can be placed between the bottom surface of transducer housing base 106 and shield base 136 during seating to prevent any air between the two and promote transmission of ultrasonic waves.

Arising out of shield base 136 is guide post 138. Guide post 138 defines at least a portion of a probe guide 139 therethrough. Probe guide 139 extends uninterrupted completely through both guide post 138 and shield base 136. Guide post 138 can include tabs as shown, or other formations such as hooks, insets, or the like that can be utilized to properly assemble shield base 136 about ultrasound transducer housing 100. In one embodiment, guide post 138 may include a removable cap (not shown) for protection of the interior sterile surface of probe guide 139 during assembly of shield 130 with ultrasound transducer housing 100.

As can be seen, shield section 132 can also include tabs 140, 142, 144, etc. that can be utilized in properly seating ultrasound housing 100 within shield 130 as well as aligning shield section 132 with shield section 134 when assembling the complete shield 130 about an ultrasound transducer housing 100.

In the illustrated embodiment, tabs 140 on shield section 132 match corresponding notch 141 on shield section 134 shown in FIG. 6. Together tabs 140 and notch 141 form a fastener that can secure shield section 132 and shield section 134 to one another. During assembly, tabs 140 can snap into notch 141 to securely fasten the two sections together and prevent separation of the sections 132, 134 during use. Of course, a shield can include additional fasteners at other locations between the two sections, or can include a single fastener at an alternative location, as would be known to one of skill in the art.

In order to disassemble shield 130, tabs 140 can be simply pinched together and slid out of notch 141. In another embodiment, a single-use fastening mechanism can be employed to secure sections of a sterilizable shield to one another. According to this embodiment, in order to disassemble a shield following use, the tabs of the fastener can be permanently disabled. For instance, tabs 140 and/or notch 141 can be permanently broken away from the shield by a pulling or twisting motion, allowing the shield sections to come apart and also ensuring that the shield, which is no longer sterile, cannot be utilized again. Any method that can ensure that a fastener can only be utilized a single time may alternatively be utilized.

Referring to FIG. 5A, the bottom of shield section 132 can be seen. The bottom surface of base 136 of section 132 includes a series of ridges 150 running along a portion of base 136. It has been found that inclusion of such ridges on the skin-contacting surface of a device can provide benefits to disclosed devices and methods. For instance, the inclusion of ridges on the skin contacting surface can push and better hold ultrasonic gel between the device and the skin surface, preventing formation of an air gap between the two and improving coupling between a subject's skin and the device. In addition, ridges along the skin contacting surface can also add an extra pushing force against the skin itself, better holding the skin tightly against the base of the transducer, and further improving contact between the device and a subject's skin, thereby further improving coupling between the subject and the device and providing an optimal ultrasound image.

Though illustrated as two ridges running along the length of the shield base, this particular arrangement is not required for the ridges. For instance, FIG. 5B illustrates another embodiment, including a plurality of ridges 150 running across the width of the bottom surface of a base 236 of a sterilizable shield. Moreover, in those embodiments in which an ultrasound transducer housing is intended for use without a sterile shield, either in a non-sterile field or in those embodiments in which the ultrasound device itself is sterilizable, ridges can be included on the skin contacting surface of the ultrasound transducer housing itself.

Ridges formed on the skin contacting surface of a device can cover the entire skin contacting surface, or only a part of the surface, as desired. For instance, the ridges can cover at least a portion of the skin contacting surface through which an ultrasonic beam is transmitted, or can also cover other portions of the skin contacting surface, and in particular, that portion in the vicinity of the probe guide (e.g., on either or both surfaces 108 and 110 of FIG. 1A). Ridges can be of particular benefit on a planar skin contacting surface, such as that illustrated in FIG. 1B, so as to encourage good contact and coupling between a subject's skin, ultrasound coupling gel, and the skin contacting surface of the device.

Ridges 150 can be formed to any size and shape and of any suitable biocompatible material that can also be, in certain embodiments, a sterilizable material. For example, ridges can have a rounded or straight edge, an individual ridge can lie in a straight line across a skin contacting surface or can curve across the surface, they can vary in height as measured from the base surface to the top edge of the ridge, multiple ridges on a single device can be identical to one another or can vary, ridges can be continuous over a surface or discontinuous, and so forth.

In one embodiment, ridges 150 can be formed of the same material as other portions of a shield or transducer housing. For instance, the entire section 132, including ridges 150 can be injection molded from a single polymeric material. In another embodiment, different portions of a sterilizable shield can be formed of different materials. For instance, ridges 150 can be formed of a polymeric material that is softer than is used to form the remainder of sterilizable shield. By way of example, a relatively soft elastomeric polymer (e.g., rubber, styrene-butadiene, soft polyurethanes, etc.) can be utilized. In such cases, ridges can be attached to a device following formation, for instance utilizing a biocompatible adhesive as is known in the art. In one embodiment, ridges can be formed on a specifically shaped component to be attached to the base of the device. For instance, a series of ridges can be formed on an ultrasound wedge as previously discussed, that can be attached either temporarily or permanently to the base of a device.

As previously stated, the sterilizable shield need not cover the entire ultrasound transducer house. For example, in one embodiment, a sterilizable shield can cover just that portion of an ultrasound transducer housing from which an ultrasonic beam can be emitted. For instance, a shield defining one or more ridges thereon can simply snap onto the base of an ultrasound transducer housing, covering that portion of the housing that will contact a user's skin.

Another beneficial feature of disclosed devices can be the geometry of a handle of a device. For instance, as previously mentioned with regard to the transducer housing, the angle at which a handle is placed on a probe device can be varied so as to obtain a more comfortable grip on the device while holding the transducer base tightly against the skin. Additional aspects of a can be improved as well. For example, as can be seen on FIG. 5A the handle of shield section 132 can include a finger grip 152 that can improve the grip of a user on the device. In other embodiments additional finger grips can be included, as desired. For instance, in one embodiment finger grips can be provided on a handle such that the handle is specifically designed for left-handed or right-handed use.

Sterilizable shield 130 also includes section 134, illustrated in FIG. 6. Section 134 can be removably attached to section 132 to enclose an ultrasound transducer housing 100, as previously discussed. Section 134 defines the terminal portion 151 of probe guide 139 in portion 160. Terminal portion 151 is sized so as to snugly reside over the top of guide post 138 of section 132 and form uninterrupted probe guide 139 extending from the top surface of portion 160 of section 134 to the bottom surface of base 136 of section 132.

It should be understood that a sterilizable shield as disclosed herein is not limited to two completely separable portions. For instance, a sterilizable shield can be hinged and/or can include additional portions, as desired. For instance, a sterilizable shield can be formed of two, three, or more separable sections that can be assembled to enclose all or a portion of an ultrasound housing and form a sterile barrier between the enclosed housing and an exterior field. In another embodiment, a sterilizable shield can be of a unitary construction. For instance, a sterilizable shield can be of a pliant material that can enclose all or a portion of an ultrasound housing and form a sterile barrier between the enclosed housing and an exterior field.

To assemble a shielded device, ultrasound transducer housing 100 defining probe guide opening 126 can be seated in shield base 136 of section 132 such that guide post 138 extends through transducer housing probe guide opening 126. As probe guide opening 126 of transducer housing 100 is slid over guide post 138, tabs on guide post 138 can slide or snap into recesses of probe guide opening 126 (not shown), helping to properly seat transducer housing 100 in section 132. After ultrasound transducer housing 100 is seated in section 132, section 134 can be aligned with section 132 and fastened into place to cover the top of transducer housing 100. If a protective cap covers the end of guide post 138, it can be removed during assembly and maintain the sterility of the interior of the probe guide 139 throughout the assembly process. Tabs 140 can snap or slide into recesses notch 141 to fasten and secure section 132 and 134 together.

Following the above described assembly process, probe guide 139 can extend continuously from the top of portion 160 of shield portion 134 through the shield base 136. Moreover, and of great benefit to the device, probe guide 139 can be sterile and within the probe guide opening 126 of ultrasound transducer housing 100.

Many procedures require a probe to remain at the subcutaneous target for a period of time following insertion of a probe. For example, during the Seldinger technique common for central venous catheter placement, a cannulated needle attached to a syringe is first guided into a vein. After the needle tip is in the lumen of the vein, the needle is held in place while a guide wire is fed down through the needle and into the vein. During this process, only a slight movement of the needle can cause the needle tip to move out of the vein, and the entire procedure must be repeated.

In order to prevent excessive motion of a probe tip following insertion to a target, one embodiment includes a clamp for the probe. In this embodiment, a device can include a clamp that can firmly hold a probe in the probe device and prevent motion of the probe during subsequent procedures such as catheter insertion, biopsy procedures, fluid aspiration, or the like. Motion of the percutaneous probe tip can be much less likely when the probe is securely clamped to the probe device and the probe device is in turn held and stabilized by pressing against the subject's skin surface as compared to when only the probe itself is held without clamping to the larger probe device.

One embodiment of a clamp for use with disclosed probe devices can be seen in FIG. 3. As can be seen, a probe 154 can extend through the probe guide of sterilizable shield 130. Clamp 156 sits atop shield section 134 such that probe 154 passes through clamp aperture 158 as shown.

Figure 7A:
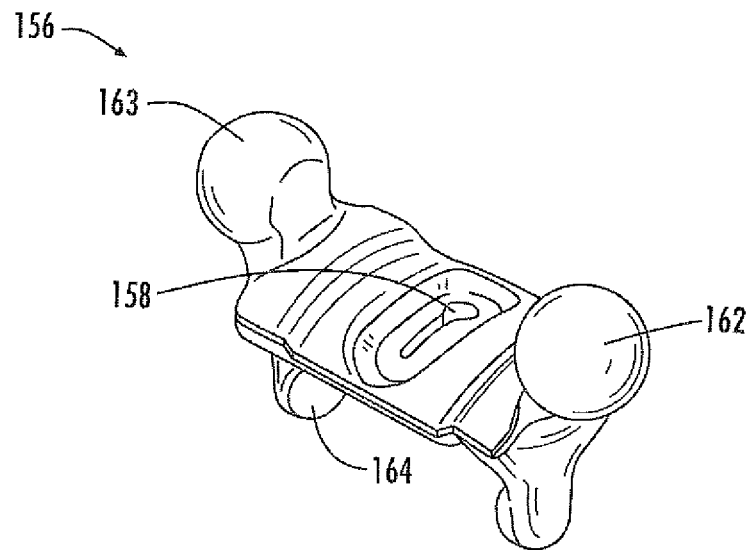
FIGS. 7A and 7B illustrate two views of the clamping mechanism of the sterilizable shield of FIG. 3.
Figure 7B:
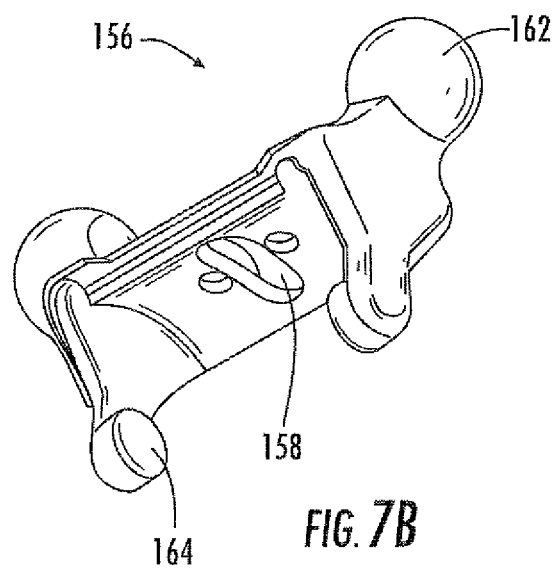

Additional details of clamp 156 can be seen with reference to FIGS. 7A and 7B. Aperture 158 includes a wide portion and a narrow portion and defines a clamping surface. The wide portion can be of a size such that a probe can pass freely through the wide portion without hindrance. Aperture 158 can gradually narrow from the wide portion of the aperture to form the narrow portion extending to a tip. Thus, when a probe is located in the wide portion of aperture 158, the clamp can be slid, rotated, or otherwise moved in relation to the probe such that the clamping portion of the clamp crosses the axis of the probe and a clamping surface of the clamp, e.g., a surface of aperture 158 at the narrow portion, can contact the probe and the probe can become tightly trapped in the narrow portion of the aperture 158 as the width of the narrow portion of aperture 158 decreases.

In another embodiment, rather than trapping a probe between two opposing clamping surfaces, as is the case for the clamp of FIGS. 7A and 7B, a clamping surface can force a probe against the wall of the probe guide to secure the probe in place. For example a clamping surface can be set on a clamp and at an angle with reference to the probe guide. Thus, as the clamp is moved and crosses the probe guide axis, the probe held in the probe guide contacts the clamping surface and becomes pressed against the wall of the probe guide by the force of the single opposing clamping surface and can be firmly gripped between the clamping surface and the wall of the probe guide. In such an embodiment, the clamping surface of the clamp need not be one side of an aperture defined by the clamp, but may be, by way of example, an outer edge of a clamp section, with no opposing piece on the clamp.

A clamp can be formed of any biocompatible, sterilizable material. For instance, in one embodiment, at least that portion of a clamp that defines a clamping surface can be formed of a material that is harder than a probe to be held by the clamp, for example a hard polymer or a stainless steel. In this embodiment, the clamping surface(s) can cut into the surface of a probe, providing additional holding power in addition to the friction hold provided by trapping the clamp with the clamping surface(s). In another embodiment, however, a clamp, and particularly a clamping surface of a clamp, can be formed of a material that is softer than a probe held in the clamp. For example, a clamp can be formed of a relatively soft polymer such as soft polyurethane or other biocompatible polymeric material. In this embodiment, the clamping surface(s) can deform somewhat as a probe is forced against the clamping surface. The deformation of a clamping surface about a probe can increase the force on the probe, more securely holding the probe in place in the clamp.

A clamp can define additional features that can improve its holding ability. For instance, a clamping surface can define a series of serrations. Upon contact between a probe and the clamping surface, the serrations of the edges can provide increased surface area for contact between the clamp and the probe, improving hold between the two. Moreover, in those embodiments in which the material forming the clamping surface is harder than that of the probe, serrations on the surface of the clamping surface can cut into the surface of the probe at the points of contact, further improving hold between the two.

Figure 8:
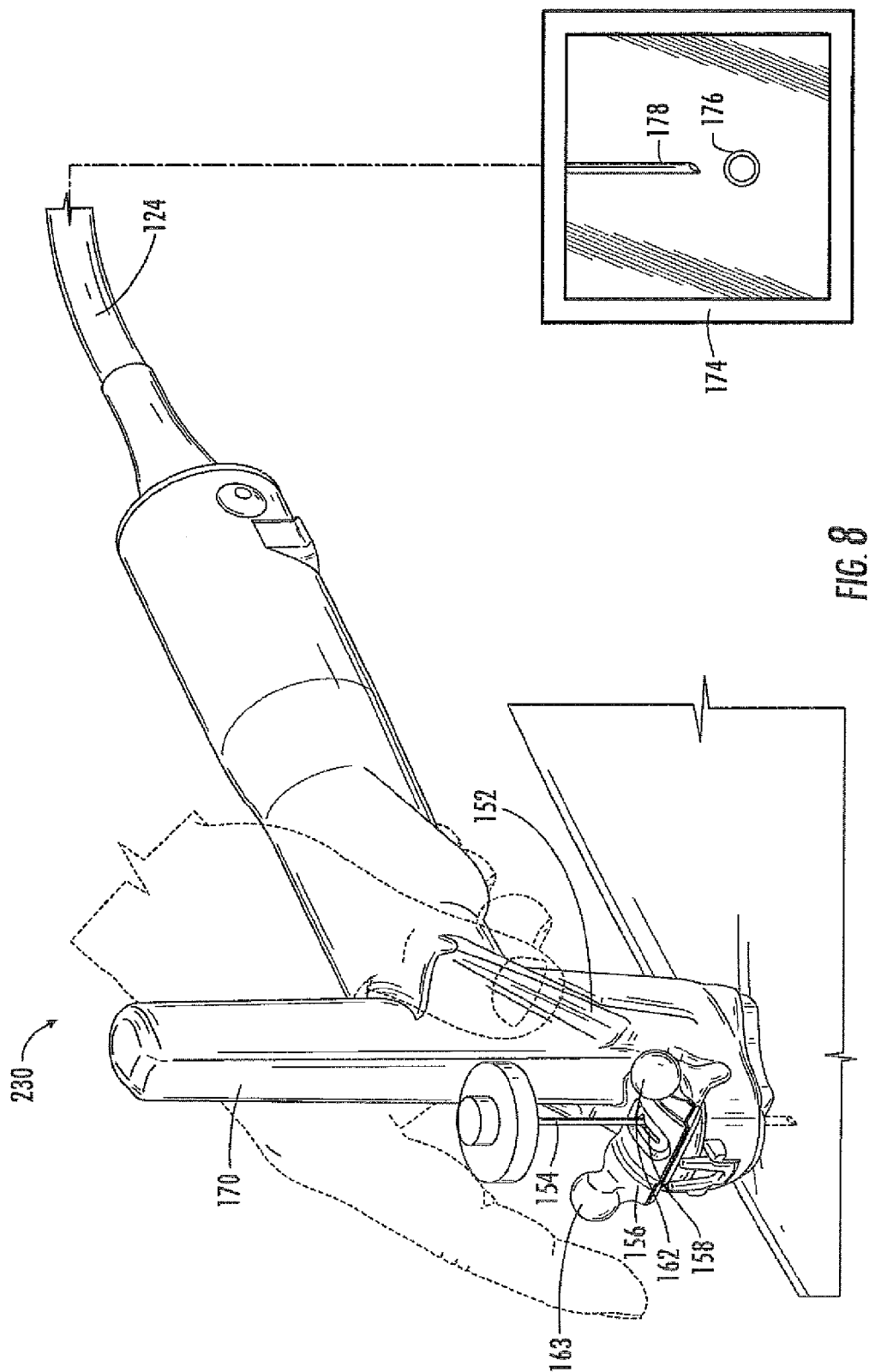
FIG. 8 illustrates one embodiment of a method for utilizing a device as disclosed herein.

Referring again to FIGS. 7A and 7B, clamp 156 includes formations 162, 163 that can be used to move clamp 156 and trap probe 154 in the aperture 158 as previously discussed. For example, as illustrated in FIG. 8, a sterilized shield 130 can be held against the skin surface of a subject and the user can move the clamp 156 with his/her thumb to force the probe into the narrow section of aperture 158 and firmly clamp the probe 154 in place.

In the illustrated embodiment, clamp 156 includes two formations 162, 163, one on either side of clamp 156 such that the clamp can be operated while held in either the right or left hand of a user. In other embodiments, clamp 156 can include only a single formation, for instance in those embodiments in which a probe device is designed for only right-handed or left-handed use, or alternatively, when the single formation can be accessed from either side of the device. Moreover, the shape of the formations 162, 163 can be any shape that can be accessed by a user and can be pushed, pulled, twisted or otherwise activated to move a clamp and tightly grip a probe in a probe guide. For example a formation can be round, as illustrated, or can be a flat, paddle-shaped formation, a post, or any other convenient shape. Moreover, any formation can be utilized to aid in moving the clamp to force a clamping surface against a probe. For instance, a clamp can define an indentation to be used in moving a clamp. In another embodiment, a clamp can define a rough tactility at a location that can aid in moving the clamp with a thumb or finger. Equivalent or alternative formations would be obvious to one of ordinary skill in the art. For instance, in another embodiment, a portion of the clamp can be rotated so as to force the clamping surface of the clamp against a probe held in the probe guide. By way of example, a probe clamp as is illustrated in U.S. Pat. No. 7,244,234 to Ridley, et al., previously incorporated by reference, can be utilized in conjunction with disclosed devices.

Referring again to FIG. 3, clamp 156 is attached to shield 130 at a pivot point. For instance, tabs 164 of clamp 156 can fit into recesses 165 formed in the lower section 132 of sterilizable shield 130 (see, e.g., FIG. 5A). During use, clamp 156 can rotate about the pivot point of tabs 164 and over the rounded upper surface of portion 160 of upper section 134 such that the clamping portion, i.e., that portion of clamp 156 that defines the aperture 158 crosses the axis of the probe 154 to lock the probe in place.

The rotation of a clamp about a pivot to secure a probe is not a requirement of disclosed clamps. For example, in another embodiment, the entire clamp can slide laterally across a portion of a probe device, e.g., a shield or a transducer housing, to clamp a probe in place. In general, any motion of all or a portion of a clamp that can be controlled by a user and can grip a probe as described is encompassed in the present disclosure.

When a probe is to be removed from a percutaneous location, or if during a procedure, a probe is to be moved from one percutaneous location to another, a projection can be moved in the opposite direction as was used to clamp the probe, freeing the probe.

FIG. 9 illustrates another embodiment of an ultrasound transducer housing 800 that can be removably attached to a sterilizable shield. According to this embodiment, ultrasound transducer housing 800 can include a handle 802, a post 804, and a base 806. Ultrasound transducer housing 800 also defines a lower surface 810, as shown. In this particular embodiment, however, the ultrasound transducer housing does not include a probe guide opening. Instead, ultrasound transducer housing 800 is removably attachable to a second portion of a device that defines a probe guide opening. For instance, ultrasound transducer housing 800 can be utilized in conjunction with a sterilizable shield that defines the probe guide. Moreover, the sterilizable shield can be formed of single or multiple removably attachable pieces.

FIGS. 10A and 10B illustrate one embodiment of a sterilizable shield 930 that can be used in conjunction with an ultrasound device 800 illustrated in FIG. 8. With reference to FIG. 10A, sterilizable shield 930 can be formed of multiple attachable pieces. Specifically, sterilizable shield 930 includes section 932 and section 961 that defines a probe guide for passage of a probe therethrough. Accordingly, section 961 can alternatively be referred to as a probe guide portion. Additionally, section 932 can be separable into two or more sections, as illustrated for device 230 of FIGS. 3-6. Section 961 can also include clamp 956 defining aperture 958 and formations 962, 963 that rotates about pivot 964 for clamping probe 954 in the probe guide. During use, section 961 can be attached to shield 932, for instance by use of aligned tabs and notches, and so forth, so as to attach the probe guide portion to the sterilizable shield, as shown in FIG. 10B.

Of course, any other arrangements of the individual portions of a device are encompassed within the present disclosure. For instance, in one embodiment, an ultrasound transducer housing that does not define a probe guide opening, as illustrated in FIG. 9, can be removably attached to a probe guide portion that can define a probe guide opening and include the clamp, without enclosing all or a portion of the ultrasound transducer housing in a shield. In another embodiment, a sterilizable shield portion can cover only the skin contacting surface of a device. For instance, a shield portion can snap onto the base of a device. In yet another embodiment, all or a portion of a sterilizable shield can be formed of a pliant material that can enclose an ultrasound transducer housing. According to such an embodiment, a probe guide portion can be indirectly attached to the pliant sterilizable shield portion, for instance by use of a frame or other attachment device that is on the pliant material or optionally on the ultrasound transducer housing itself, such that the pliant material of the shield is held between the frame and the probe guide portion.

Figure 11:
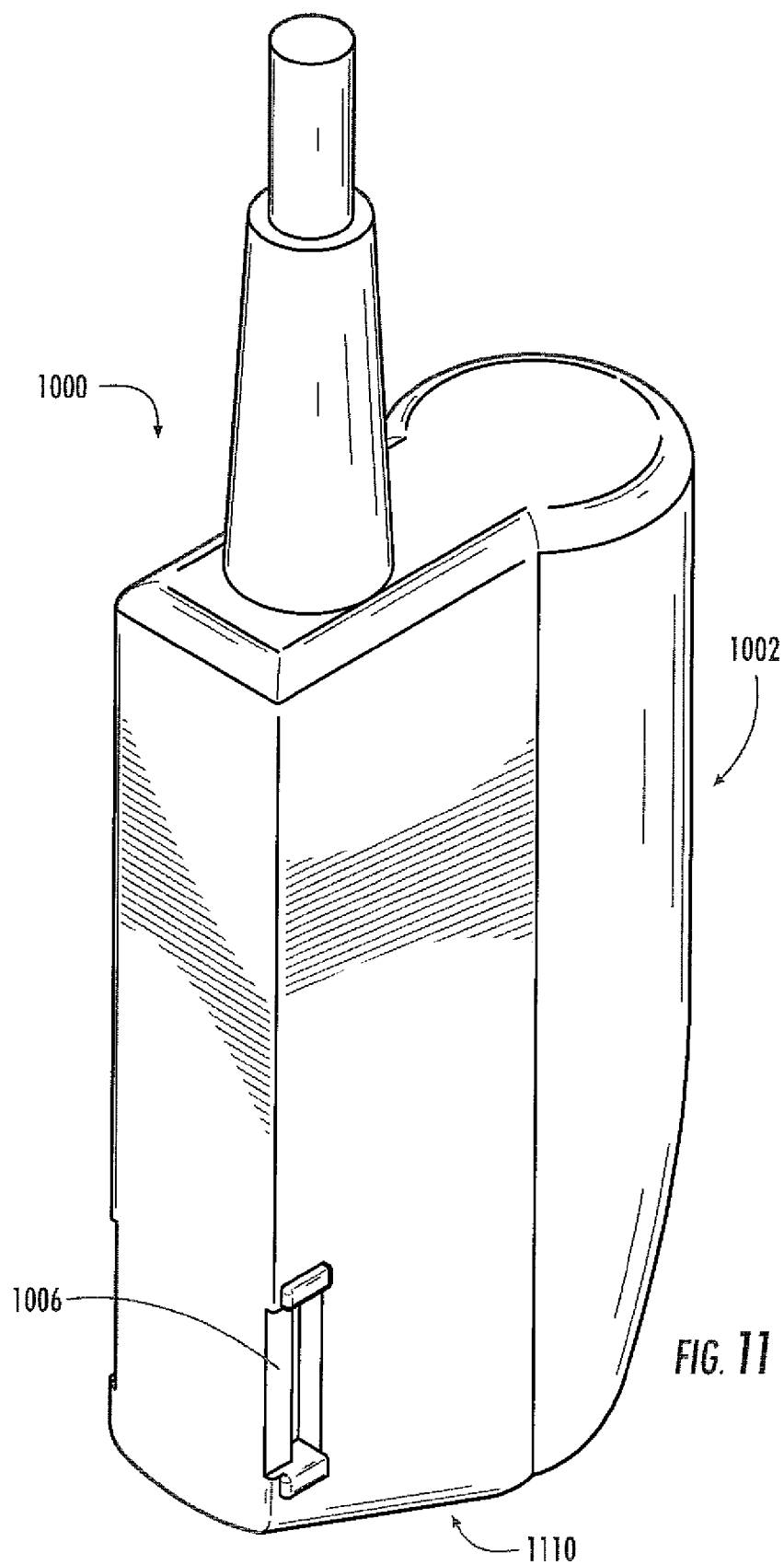
FIG. 11 illustrates another embodiment of a probe device as disclosed herein.

Yet another embodiment is illustrated in FIG. 11. As can be seen according to this embodiment, a device 1000 need not include a separate handle portion. Such a device can be comfortably held by the rounded back portion 1002, while holding the angled skin contacting surface 1110 against a subject.

Figure 12:
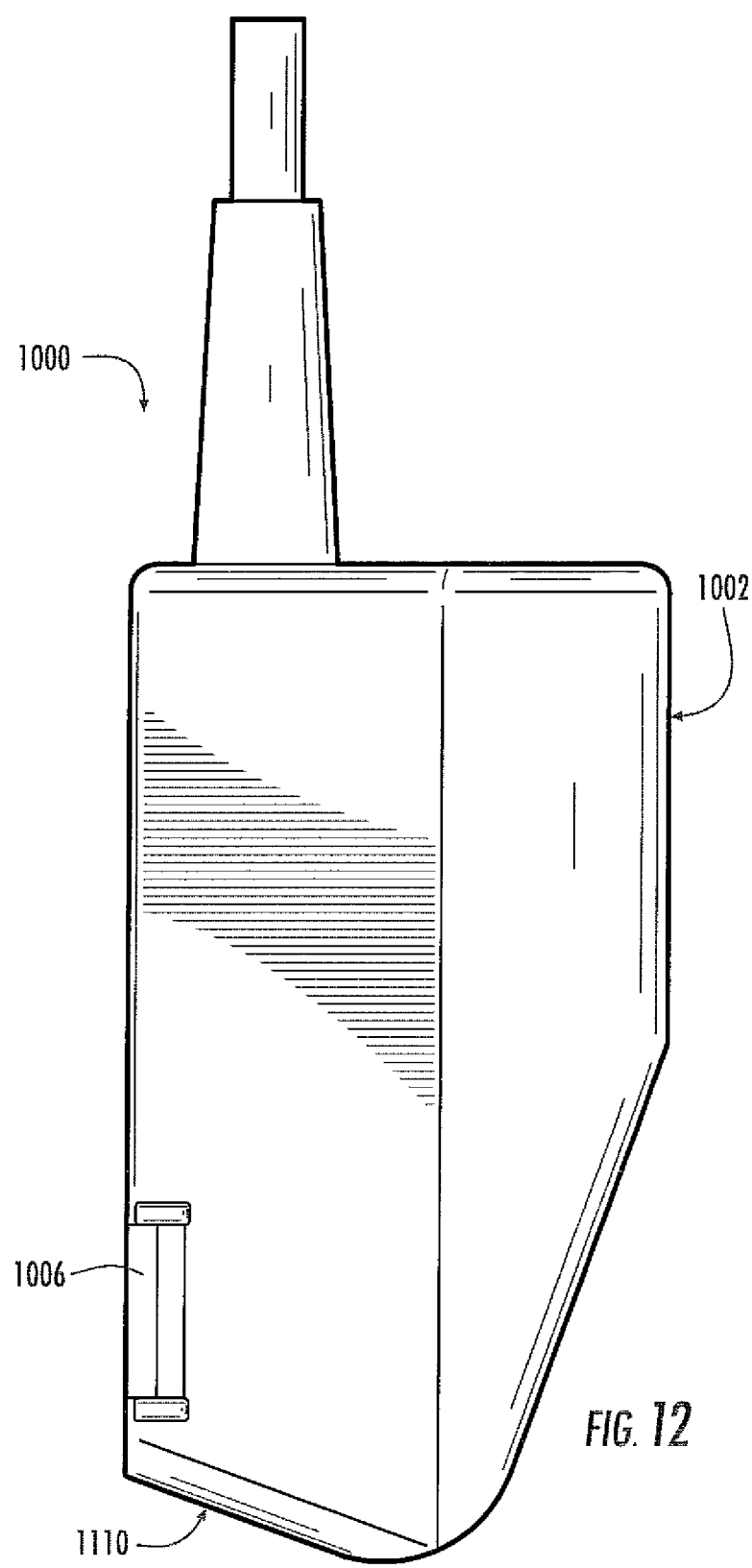
FIG. 12 is a side view of the probe device illustrated in FIG. 11.

A side view of device 1000 shown in FIG. 12 better illustrates the angle of skin contacting surface 1110. Of course, as discussed above, a device need not include an angle in the skin contacting surface, and in another embodiment the skin contacting surface of a device can be flat with no angle as is shown for the device of FIG. 11, or arcuate.

Figure 13:
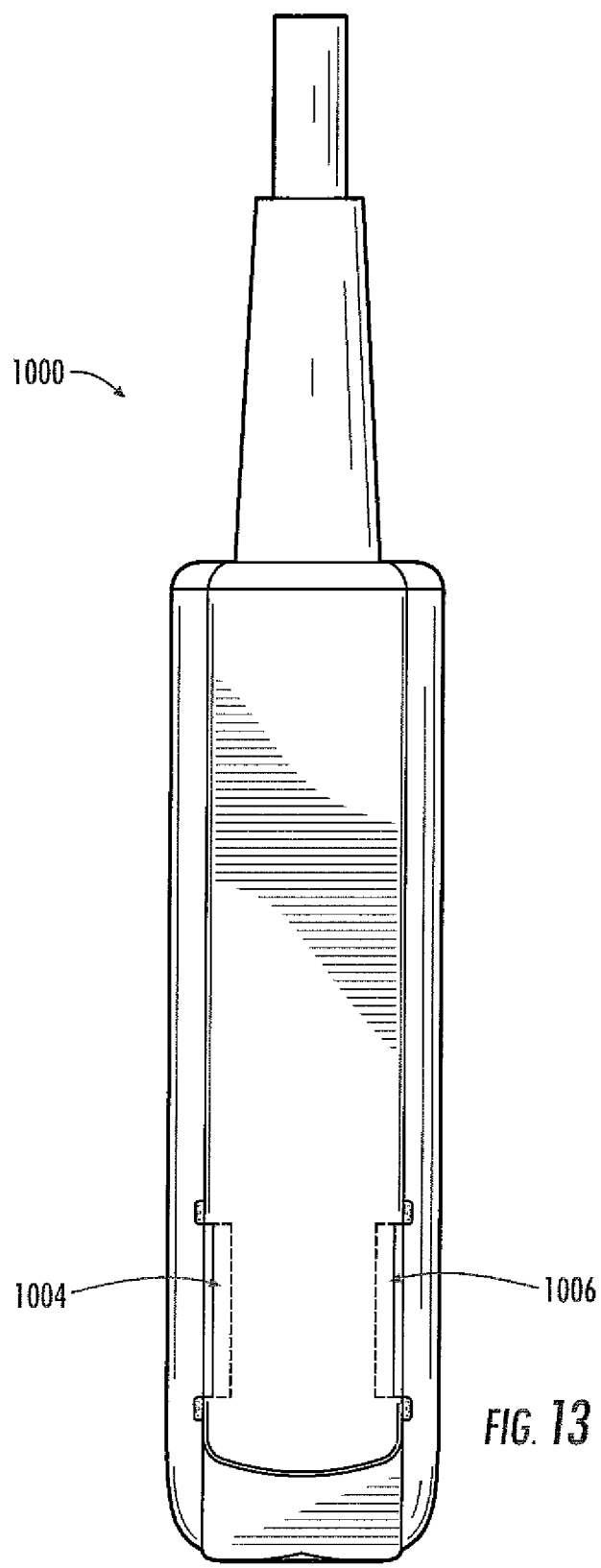
FIG. 13 is a front view of the probe device illustrated in FIG. 11.
Figure 14:
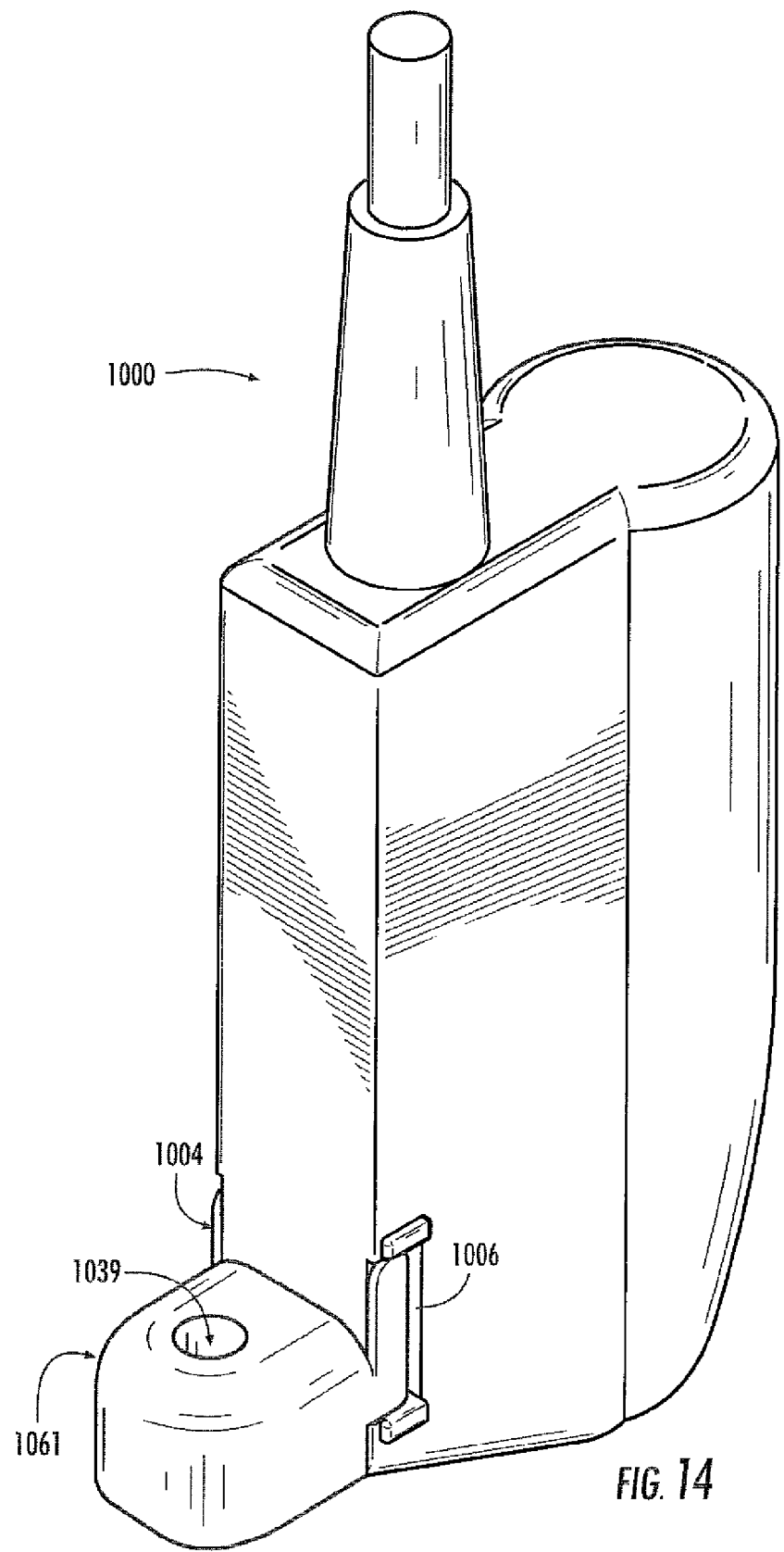
FIG. 14 illustrates the device of FIG. 11 including a removably attachable probe guide portion.
Figure 15:
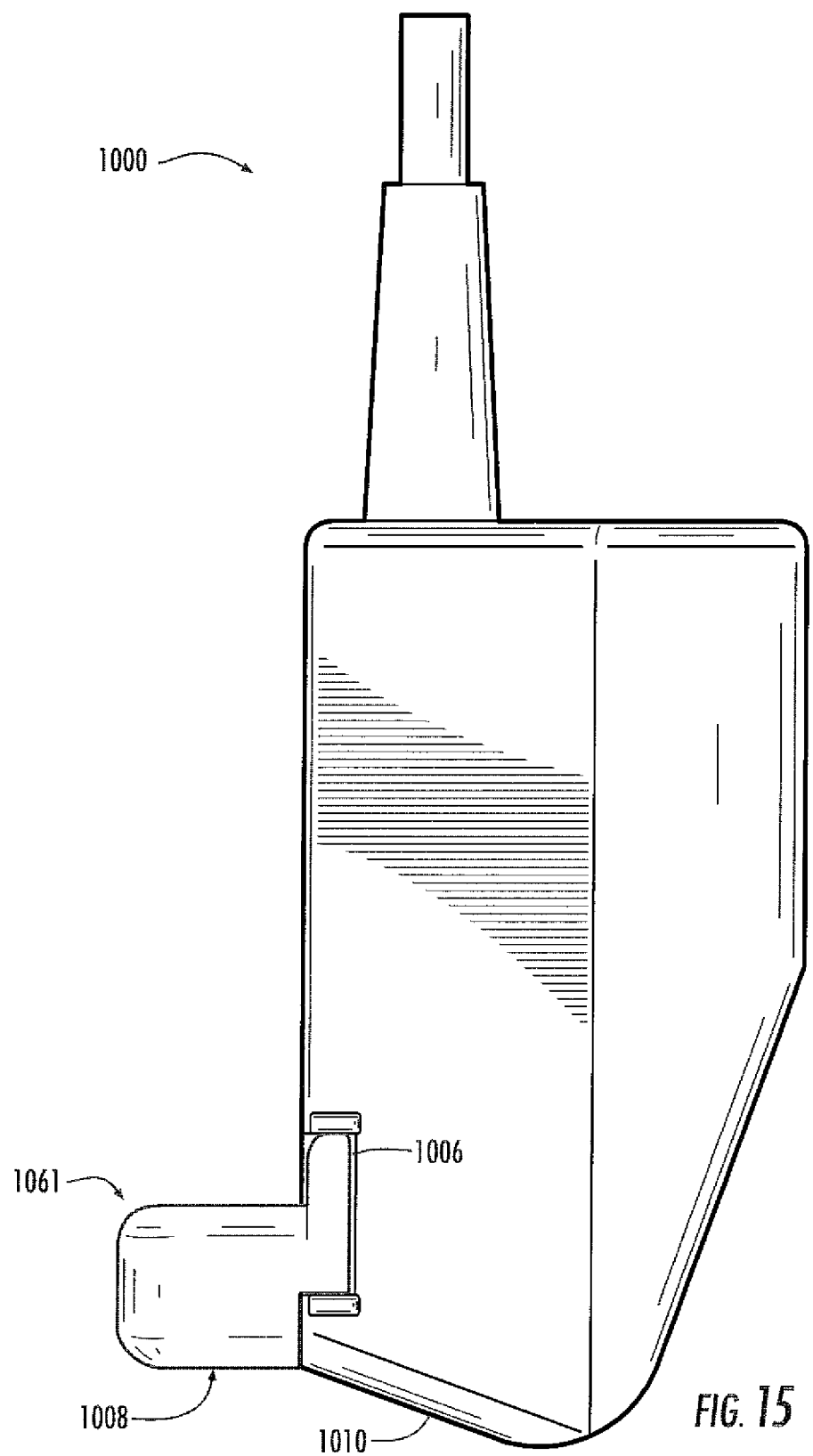
FIG. 15 is a side view of the device of FIG. 14.
Figure 16:
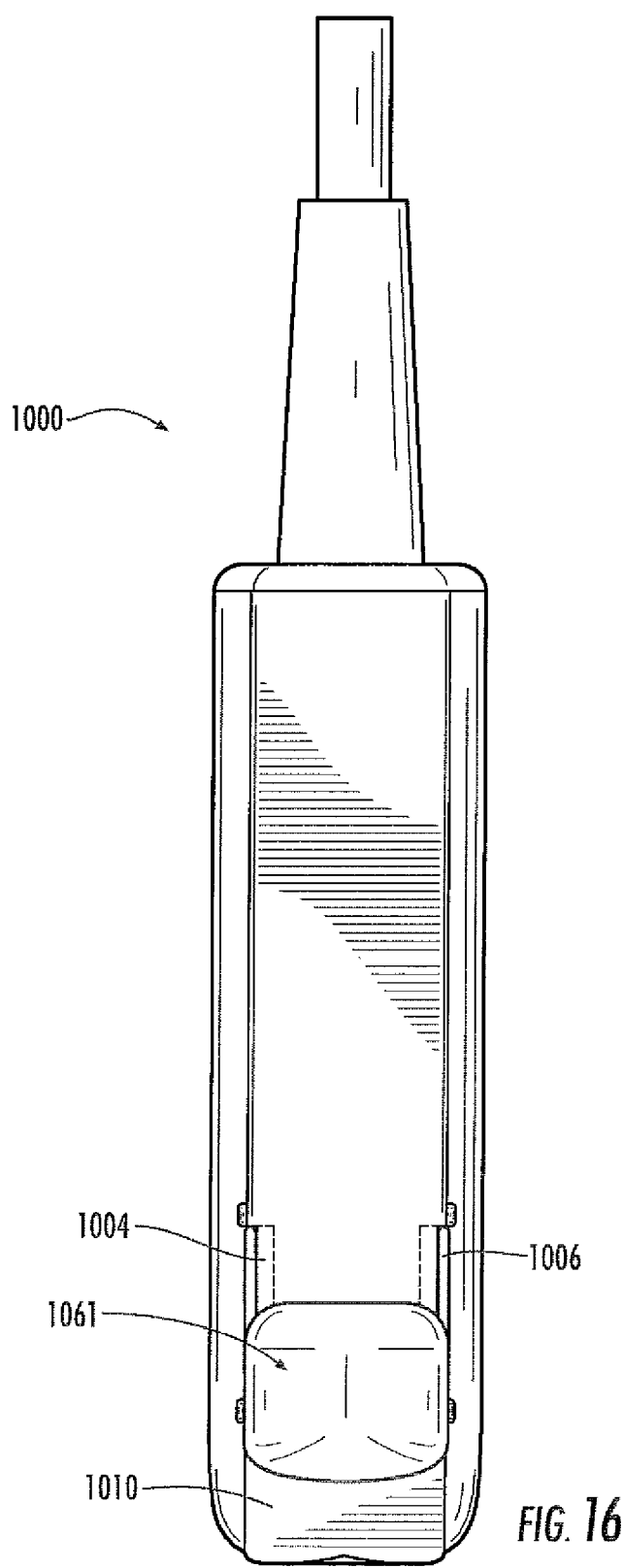
FIG. 16 is a front view of the device of FIG. 14.

A front view of device 1000 is shown in FIG. 13. As can be seen, device 1000 includes attachment slots 1004, 1006 on either side of the device. These attachment slots 1004, 1006 can be utilized to attach another portion to device 1000. For example, FIG. 14 illustrates device 1000 including a probe guide portion 1061 attached to device 1000 via slots 1004, 1006. When attached, probe guide portion 1061 can, in one embodiment, be attached such that probe guide 1039 is aligned with an ultrasound transducer located in the base of device 1000. Of course, device 1000 need not include an ultrasound transducer in the base. FIG. 15 illustrates a side view of device 1000 including probe guide portion 1061 attached thereto. As can be seen, probe guide portion 1061 can define skin contacting surface 1008 and device 1000 can device skin contacting surface 1010, with the two surfaces 1008, 1010 held at an angle to one another to promote improved contact between a device and a subject, as previously discussed. FIG. 16 is a front view of the embodiment illustrated in FIGS. 14 and 15.

In one embodiment, all or a portion of device 1000 can be covered or encased with a sterilizable shield. For instance all of the body 1000 of the device can be encased in a sterilizable shield, and the probe guide portion 1061 can then be attached to the sterilizable shield. Alternatively, one a portion of the device, for instance the skin contacting portion, can be covered by a sterilizable shield. In one embodiment, the probe guide portion 1061 can be sterile, and the portion 1000 can be nonsterile.

In one embodiment, a probe guide portion need not include a skin contacting surface. For instance, a separably removable probe guide portion can be attached to a device such that the base of the probe guide portion will be above and not contacting the skin of a subject. According to this embodiment, contact between a subject and a device will only be between the body of a device that encompasses the ultrasound transducer. For instance, when the body of a device incorporates an ultrasound transducer therein, the skin contacting surface can be at the surface from which an ultrasonic beam is emitted, and the probe guide portion can be aligned with the transducer, but held above the skin contacting surface of the body of the device. In this embodiment, a probe passing through a probe guide will exit the probe guide and pass for a distance through the surrounding air prior to contacting the skin of a subject and passing therethrough.

Additionally, though illustrated in FIG. 14 with probe guide portion 1061 completely defining and surrounding the probe guide 1039 that passes therethrough, this is not a requirement of the present disclosure. For example, in another embodiment, a probe guide can be defined between a probe guide portion 1061 and the side of device 1000. According to this embodiment, a probe guide portion can define a V-shaped notch, a slot, a semi-circular cut out or the like in the side of the probe guide portion that will contact the device 1000. Upon attachment of the probe guide portion to the body of the device, the probe guide can be completely formed. Moreover, the side of the body of the device can also define a portion of a probe guide, in one embodiment, and the probe guide can be formed between the two removably attachable portions of the device.

A probe guide portion can also be formed of multiple removably attachable pieces, if desired.

Figure 17:
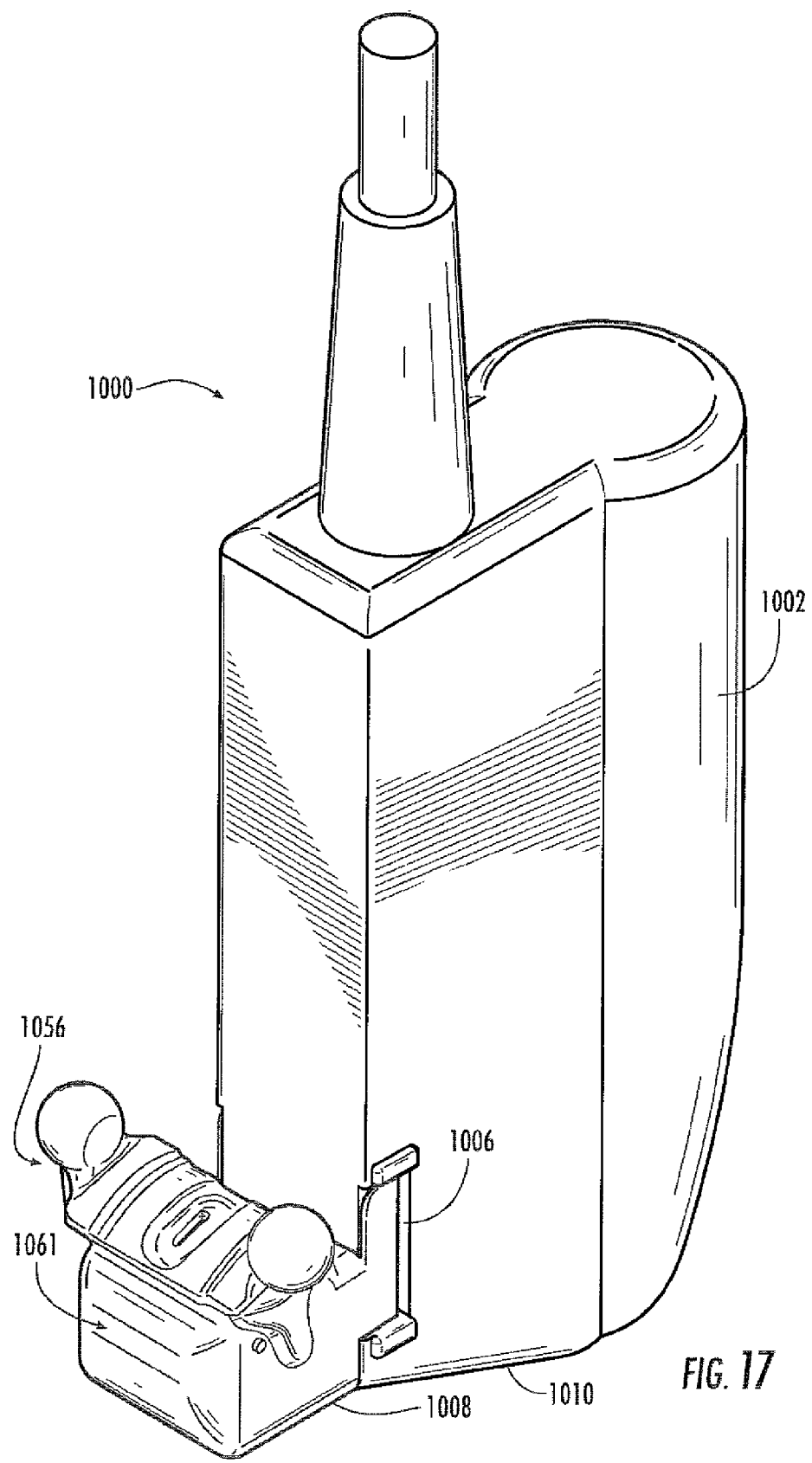
FIG. 17 illustrates the device of FIG. 14 with a clamp removably attached to the probe guide portion.
Figure 18:
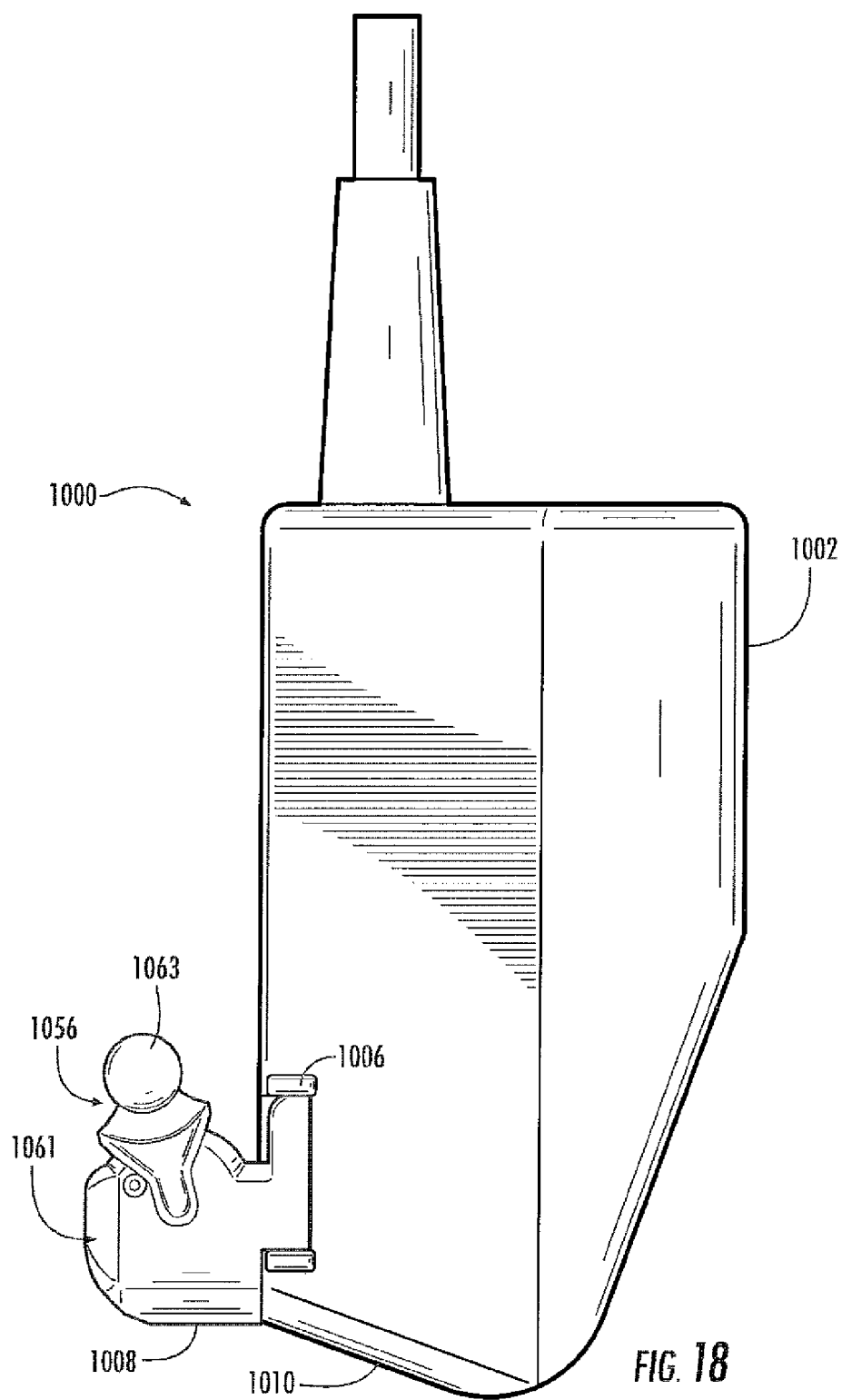
FIG. 18 is a side view of the device of FIG. 17.
Figure 19:
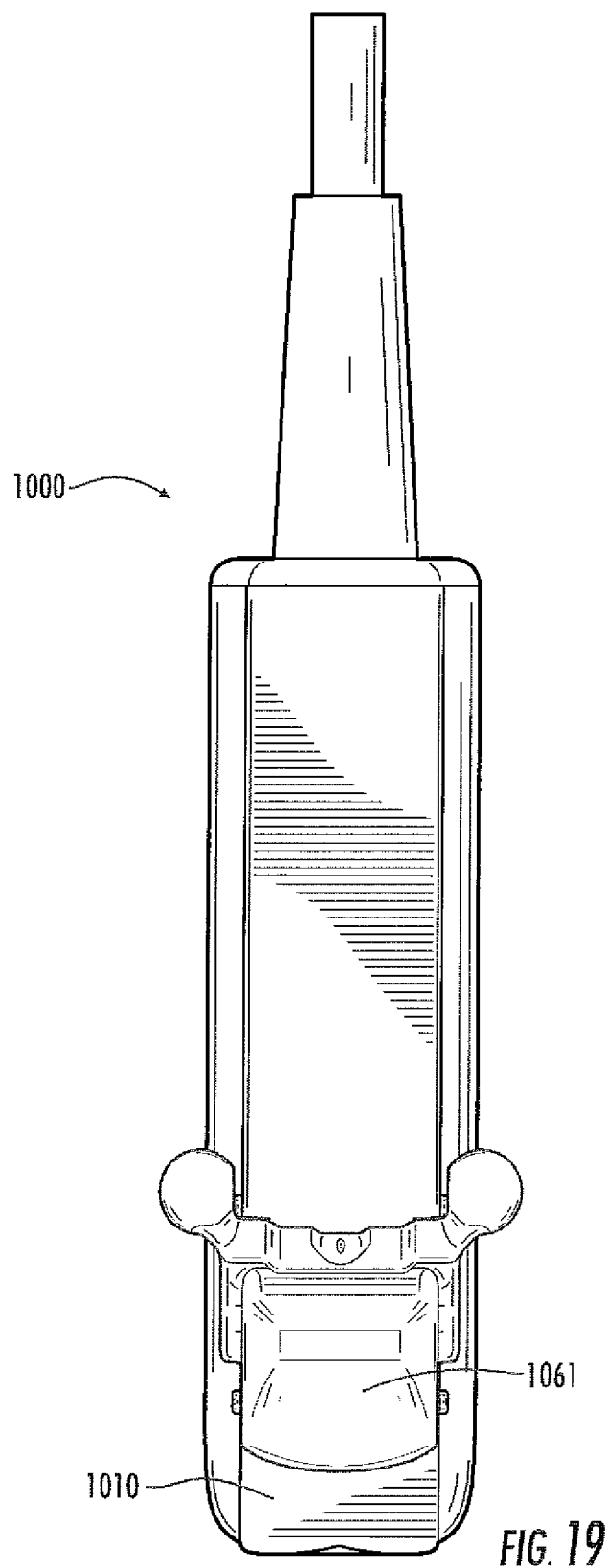
FIG. 19 is a front view of the device of FIG. 17.

FIG. 17 illustrates the device 1000 following attachment of a clamp 1056 to the probe guide portion 1061. FIG. 17 illustrates this embodiment in a side view and FIG. 18 illustrates this embodiment in a front view. During use, a device can be held against the skin and a probe can be passed through the probe guide. Upon reaching the desired subdermal location, the clamp 1056 can be activated, for instance by the user pulling formation 1063 from the unclamped to the clamped position.

Utilizing presently disclosed devices, a probe tip can be guided to a percutaneous target on a line that is parallel to the plane imaged on a sonogram formed by use of an ultrasound transducer incorporated in a device. For instance, the probe tip can travel on a path that defines a line that is coincident in the scanned plane, is parallel to the scanned plane, or intersects the scanned plane at a point. When utilizing the presently disclosed devices, the path of the probe to the target can be known, even if it cannot be discerned on the sonogram: the probe will advance toward the target on a straight line and at a predetermined angular relationship to the ultrasound housing base from the probe guide opening to the target that is imaged by the ultrasound. Thus, the path of the probe and the scanned plane of the sonogram image can both be defined by the orientation of the transducer and can be coordinated on the target. In order to strike the target, the probe can be merely guided along this known path the desired distance.

In an ideal situation, the probe itself can be visualized on the scanned plane. For instance, in those embodiments in which the path of the probe is on a line within the scanned plane, the probe can be seen in the sonogram, depending on the density of surrounding tissue and other process parameters. However, in one embodiment, even if the path of the probe is coincident with the scanned plane, the probe itself may not be visible on the sonogram, but artifacts of the passage of the probe can be visualized, e.g., shadows, motions of internal structures as the probe passes, and so forth.

In one preferred embodiment, the known path of the probe can be added to the sonogram, and the targeting procedures can be even further simplified. For example, one embodiment includes the addition of a targeting line on the sonogram extending from that point on the sonogram where the probe guide opening exits the housing (or passes the transducer) and projecting across the ultrasonic field in a straight line at the known angle. Thus, if this targeting line is made to intersect the target that is imaged by the device, the operator can be confident that the probe is accurately directed to the target. In other embodiments, other targeting information can be displayed on the sonogram. For example, in one embodiment, information showing the approach of the probe to the target can be displayed.

In one particular embodiment, a motion detector can register motion of a probe in the probe guide, and that information can be displayed, for instance, as a real time image of the probe on a screen or monitor. In this embodiment, the location of the probe tip in relation to the target and the moment when the probe tip strikes the target can be seen in real time by an operator watching the virtual probe on the monitor during the procedure.

FIG. 8 illustrates one embodiment of the presently disclosed subject matter during use in which an image of a virtual probe may be overlaid on a sonogram. In this particular embodiment, the probe device can include a detector 170 located in the post of the sterilizable shield or in the post of the transducer housing. Detector 170 can recognize and monitor the movement of probe 154 as it passes through probe guide and into a subject. Information from detector 170 and the ultrasound transducer can pass through cable 124 to monitor 174. The probe 154 can then be imaged on a monitor 174 as probe image 178. The monitor 174 can also show the internal target, for instance a blood vessel 176.

A variety of different possible detectors as are generally known in the art may be utilized as detector 170. For instance, detector 170 can utilize infrared (IR), ultrasound, optical, laser, magnetic or other motion detection mechanisms. In addition, the location of detector 170 is not critical to the invention. In the embodiment illustrated in FIG. 8, detector 170 is located in the post of either the shield 130 or the ultrasound transducer housing enclosed within the shield 130. In other embodiments, however, the detector may be located elsewhere in the system including, for example, on a portion of the probe itself.

Signals from detector 170 can create a data stream which can be sent to a processor. A processing unit can be internal or external to the hand-held device. For example, data from detector 170 can be sent to a standard lap top or desk top computer processor or part of a self-contained ultrasound system as is known in the art. A processor can be loaded with suitable recognition and analysis software and can receive and analyze the stream of data from detector 170. The processing unit can also include standard imaging software as is generally known in the art to receive data from the ultrasound transducer via cable 124. Probe 154 can be of a predetermined length which can be input data entered into a processor by the user or can be preprogrammed into the system as default data. Thus, through analysis of the data stream received from detector 170 and from ultrasound transducer 120, a processor can be programmed to calculate the relative position of the probe tip in relation to the ultrasound transducer 120, in relation to detector 170, in relation to the exit of the probe guide, or to any other convenient reference point. A processor can communicate this position information digitally to monitor 174 and the information can be displayed on the monitor such as in a numerical format or optionally as a real time image of a virtual probe 178 shown in conjunction with the sonogram including an image 176 of the target, such as a blood vessel.

In such a manner, disclosed devices can be utilized to actually show the approach of the probe toward the target on the monitor throughout the entire procedure. In addition, in certain embodiments, disclosed devices can be utilized to ensure the probe tip remains at the target during subsequent procedures. For example, in those embodiments wherein the detector 170 monitors the motion of the probe 154, as long as probe 154 remains 'visible' to detector 170, the image 176 of probe 154 can remain on the monitor 174. Thus, any motion of the probe tip in relation to the target can be noted by an observer.

The presently disclosed ultrasound guided probe devices and methods may be utilized in many different medical procedures. Exemplary applications for the devices can include, without limitation Central Venous Catheterization
Cardiac Catheterization (Central Arterial Access)
Dialysis Catheter Placement
Breast Biopsies
Paracentesis
Pericardiocentesis
Thoracentesis
Arthrocentesis
Lumbar Puncture
Epidural Catheter Placement
Peripherally Inserted Central Catheter (PICC) line placement Thyroid Nodule Biopsies
Cholecystic Drain Placement
Amniocentesis
Regional Anesthesia—Nerve Block Some of these exemplary procedures have employed the use of ultrasound in the past, and all of these procedures, as well as others not specifically listed, could utilize the disclosed ultrasound guided devices to improve procedural safety as well as patient safety and comfort, in addition to provide more economical use of ultrasound devices. In addition, the presently disclosed devices may be utilized with standard probe kits already available on the market.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A medical probe device comprising:
a monitor;
a housing comprising an ultrasound transducer for forming a sonogram of a subdermal location on the monitor, the housing including a skin contacting surface;
a probe guide that is attachable to the housing;
a detector for detecting motion of a probe within the probe guide, the detector including a magnetic motion detection mechanism to generate signals regarding the movement of a probe as it passes through the probe guide, the signals from the detector creating a data stream;
a processor in communication with the detector, the monitor, and the ultrasound transducer, the processer configured for creating and displaying a real time image of a virtual probe, the processor being programmed to analyze the data stream from the detector to calculate a relative position of the probe in relation to a reference point, the processor being capable of communicating the relative position to the monitor, said relative position being displayed on the monitor as the real time image of the virtual probe; and
the processor being further configured for displaying on the monitor the real time image of the virtual probe in conjunction with the sonogram of the subdermal location.

2. The medical probe device of claim 1, the skin contacting surface comprising a first portion and a second portion that are removably attachable to one another.

3. The medical probe device of claim 2, the first portion defining a first plane and the second portion defining a second plane, the first plane and the second plane intersecting one another to define an angle therebetween that is greater than about 150° and less than 180°.

4. The medical probe device of claim 1, further comprising a clamp for clamping a probe in the probe guide.

5. The medical probe device of claim 1, further comprising at least one raised ridge on the skin contacting surface.

6. The medical probe device of claim 1, further comprising a single-use sterilizable shield that is attachable to the housing.

7. The medical probe device of claim 6, wherein the single use shield comprises a first section and a second section that are attachable to one another.

8. The medical probe device of claim 7, wherein the second section defines the probe guide therethrough.

9. The medical probe device of claim 7, wherein the first section and the second section are attachable to one another by a fastener that is a single-use fastener.

10. A method for visualizing a probe on a sonogram comprising:
guiding a probe through a probe guide to a subdermal location wherein the probe guide is attached to an ultrasound transducer housing;
utilizing an ultrasound transducer to form a sonogram of the subdermal location on a monitor, the ultrasound transducer housin containin the ultrasound transducer;
detecting the motion of the probe within the probe guide by use of a detector, the detector utilizing a magnetic motion detection mechanism;
creating a data stream in response to the detected motion within the probe guide;
utilizing a processing unit that is in communication with the detector, the monitor, and the ultrasound transducer to process information contained in the data stream to form a real time image of a virtual probe on the monitor, the processing unit being programmed to calculate a relative position of the probe in relation to a reference point, the processing unit being capable of communicating the relative position to the monitor, the relative position being displayed on the monitor as the real time image of the virtual probe; and
displaying on the monitor the sonogram and the real time image of the virtual probe, the real time image of the virtual probe being displayed in conjunction with the sonogram, 11. The method of claim 10, wherein the ultrasound transducer housing comprises a first portion and a second portion that are removably attachable to one another.

12. The method of claim 11, wherein the first portion comprises the probe guide and the second portion comprises the ultrasound transducer.

13. The method of claim 10, the method further comprising clamping the probe in the probe guide.

14. The method of claim 10, the method further comprising enclosing the transducer in a sterilizable shield.

15. The method of claim 14, wherein the sterilizable shield is a single-use sterilizable shield.

16. The method of claim 14, wherein the sterilizable shield comprises multiple sections, the method further comprising attaching the sections of the sterilizable shield to one another.

* * * * *

UNITED STATES PATENT AND TRADEMARK OFFICE
CERTIFICATE OF CORRECTION

| | | |
|---|---|---|
| PATENT NO. | : 8,761,862 B2 | Page 1 of 1 |
| APPLICATION NO. | : 12/576487 | |
| DATED | : June 24, 2014 | |
| INVENTOR(S) | : Stephen F. Fidley and M. Dexter Hagy | |

It is certified that error appears in the above-identified patent and that said Letters Patent is hereby corrected as shown below:

In the Claims

In claim 10, Column 18, Line 21-22, there is a missing comma after the word "location" should read -- "...location, wherein the probe guide is attached to an ultrasound..." --

In claim 10, Line 25, "housing containing" should read -- "...transducer housing containing the ultrasound transducer..." --

In claim 10, Line 44, should end with period instead of a comma. -- "... sonogram." --

Signed and Sealed this

Thirteenth Day of January, 2015

Michelle K. Lee
*Deputy Director of the United States Patent and Trademark Office*